United States Patent
Aravamudan et al.

(10) Patent No.: US 12,229,962 B1
(45) Date of Patent: Feb. 18, 2025

(54) APPARATUS AND METHOD FOR LEVERAGING A REPOSITORY OF IMAGES CONTAINING IMPLANT DEVICES IN A HUMAN BODY

(71) Applicant: nference, Inc., Cambridge, MA (US)

(72) Inventors: Murali Aravamudan, Andover, MA (US); Ajit Rajasekharan, West Windsor, NJ (US)

(73) Assignee: nference, Inc., Cambridge, MA (US)

(*) Notice: Subject to any disclaimer, the term of this patent is extended or adjusted under 35 U.S.C. 154(b) by 0 days.

(21) Appl. No.: 18/808,442

(22) Filed: Aug. 19, 2024

(51) Int. Cl.
*G06K 9/00* (2022.01)
*G06T 7/00* (2017.01)
(Continued)

(52) U.S. Cl.
CPC .............. *G06T 7/0016* (2013.01); *G06T 7/74* (2017.01); *G16H 50/70* (2018.01); *G06T 2200/24* (2013.01); *G06T 2207/20081* (2013.01); *G06T 2207/20084* (2013.01); *G06T 2207/30052* (2013.01)

(58) Field of Classification Search
CPC . G06T 2207/30052; G06T 2207/10068; G06T 7/70–77; G06T 7/0012–0016; G06T 2207/10064–10136; G06T 2207/30004–30104; G06T 2207/10072–10128; G06T 11/60; G06T 2207/30176; G06T 2207/20081; A61B 34/00–77; A61B 1/313–317; G06V 2201/03–034; G06V 30/40–43; G06V 30/10–387; G06V 10/774; G06F 16/58; G06F 16/583; G06F 16/5846; G06F 40/00–58; G06F 18/214–2155; G06F 7/023; G06F 40/16; G06N 3/08–0985
See application file for complete search history.

(56) References Cited

U.S. PATENT DOCUMENTS

| | | | |
|---|---|---|---|
| 12,056,443 B1* | 8/2024 | Jaiswal | G06F 40/169 |
| 2020/0074631 A1* | 3/2020 | Giancardo | A61B 5/0082 |

(Continued)

FOREIGN PATENT DOCUMENTS

| | | |
|---|---|---|
| CN | 113592769 A | 4/2024 |
| EP | 4154819 A1 | 3/2023 |
| WO | 2007009263 A1 | 1/2007 |

*Primary Examiner* — Atiba O Fitzpatrick
(74) *Attorney, Agent, or Firm* — Caldwell Intellectual Property Law

(57) ABSTRACT

An apparatus method for leveraging a repository of images containing implant devices in a human body are disclosed. The apparatus includes at least a processor and a memory communicatively connected to the at least a processor, wherein the memory contains instructions configuring the at least a processor to receive a plurality of sets of historical subject data, classify the plurality of sets of historical subject data into one or more implant cohorts, generate implant training data using the plurality of sets of classified historical subject data in the one or more implant cohorts, train an implant machine-learning model using the implant training data, receive an inquiry datum from a user, wherein the inquiry datum includes current subject data and generate an output datum as a function of the inquiry datum using the trained implant machine-learning model.

20 Claims, 10 Drawing Sheets

(51) Int. Cl.
*G06T 7/73* (2017.01)
*G16H 50/70* (2018.01)

(56) References Cited

U.S. PATENT DOCUMENTS

| | | | |
|---|---|---|---|
| 2020/0381120 A1* | 12/2020 | Isaacson | A61B 8/0841 |
| 2021/0338387 A1* | 11/2021 | Inam | G06T 7/0012 |
| 2021/0343400 A1* | 11/2021 | Inam | G16H 40/67 |
| 2023/0018833 A1* | 1/2023 | Das | G16H 50/70 |
| 2023/0053280 A1* | 2/2023 | Yoo | A61B 5/7264 |
| 2024/0104727 A1* | 3/2024 | Weede | G16H 30/40 |
| 2024/0164845 A1* | 5/2024 | Tegzes | A61B 6/54 |
| 2024/0206821 A1* | 6/2024 | Upadhyay | A61B 5/318 |
| 2024/0274301 A1* | 8/2024 | Awasthi | G16H 50/70 |

\* cited by examiner

APPARATUS AND METHOD FOR LEVERAGING A REPOSITORY OF IMAGES CONTAINING IMPLANT DEVICES IN A HUMAN BODY

FIELD OF THE INVENTION

The present invention generally relates to the field of medical images. In particular, the present invention is directed to an apparatus and method for leveraging a repository of images containing implant devices in a human body.

BACKGROUND

The increasing prevalence of medical implants has significantly improved the quality of life for many patients by restoring function and alleviating pain in various parts of the body. Modem medical imaging modalities, including X-rays, CT (Computed Tomography) scans, MRI (Magnetic Resonance Imaging) scans, and ultrasound, play a pivotal role in capturing high-resolution images that illustrate both the anatomical structures and the implanted devices. Despite the advancements in imaging technology, the manual interpretation of these images remains a time-consuming and error-prone process.

SUMMARY OF THE DISCLOSURE

In an aspect, an apparatus for leveraging a repository of images containing implant devices in a human body is disclosed. The apparatus includes at least a processor and a memory communicatively connected to the at least a processor, wherein the memory contains instructions configuring the at least a processor to receive a plurality of sets of historical subject data, wherein the plurality of sets of historical subject data includes historical image data and historical textual data related to an implant device implanted in a subject's body, classify the plurality of sets of historical subject data into one or more implant cohorts, generate implant training data using the plurality of sets of classified historical subject data in the one or more implant cohorts, wherein the implant training data includes exemplary historical image data correlated to exemplary historical textual data, train an implant machine-learning model using the implant training data, receive an inquiry datum from a user, wherein the inquiry datum includes current subject data and generate an output datum as a function of the inquiry datum using the trained implant machine-learning model, wherein the output datum is related to a position of the implant device.

In another aspect, a method for leveraging a repository of images containing implant devices in a human body is disclosed. The method includes receiving, using at least a processor, a plurality of sets of historical subject data, wherein the plurality of sets of historical subject data includes historical image data and historical textual data related to an implant device implanted in a subject's body, classifying, using the at least a processor, the plurality of sets of historical subject data into one or more implant cohorts, generating, using the at least a processor, implant training data using the plurality of sets of classified historical subject data in the one or more implant cohorts, wherein the implant training data includes exemplary historical image data correlated to exemplary historical textual data, training, using the at least a processor, an implant machine-learning model using the implant training data, receiving, using the at least a processor, an inquiry datum from a user, wherein the inquiry datum includes current subject data and generating, using the at least a processor, an output datum as a function of the inquiry datum using the trained implant machine-learning model, wherein the output datum is related to a position of the implant device.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatuses and methods for leveraging a repository of images containing implant devices in a human body are disclosed. The apparatus includes at least a processor and a memory communicatively connected to the at least a processor, wherein the memory contains instructions configuring the at least a processor to receive a plurality of sets of historical subject data, wherein the plurality of sets of historical subject data includes historical image data and historical textual data related to an implant device implanted in a subject's body, classify the plurality of sets of historical subject data into one or more implant cohorts, generate implant training data using the plurality of sets of classified historical subject data in the one or more implant cohorts, wherein the implant training data includes exemplary historical image data correlated to exemplary historical textual data, train an implant machine-learning model using the implant training data, receive an inquiry datum from a user, wherein the inquiry datum includes current subject data and generate an output datum as a function of the inquiry datum using the trained implant machine-learning model, wherein the output datum is related to a position of the implant device. Exemplary embodiments illustrating aspects of the present disclosure are described below in the context of several specific examples.

Figure 1:
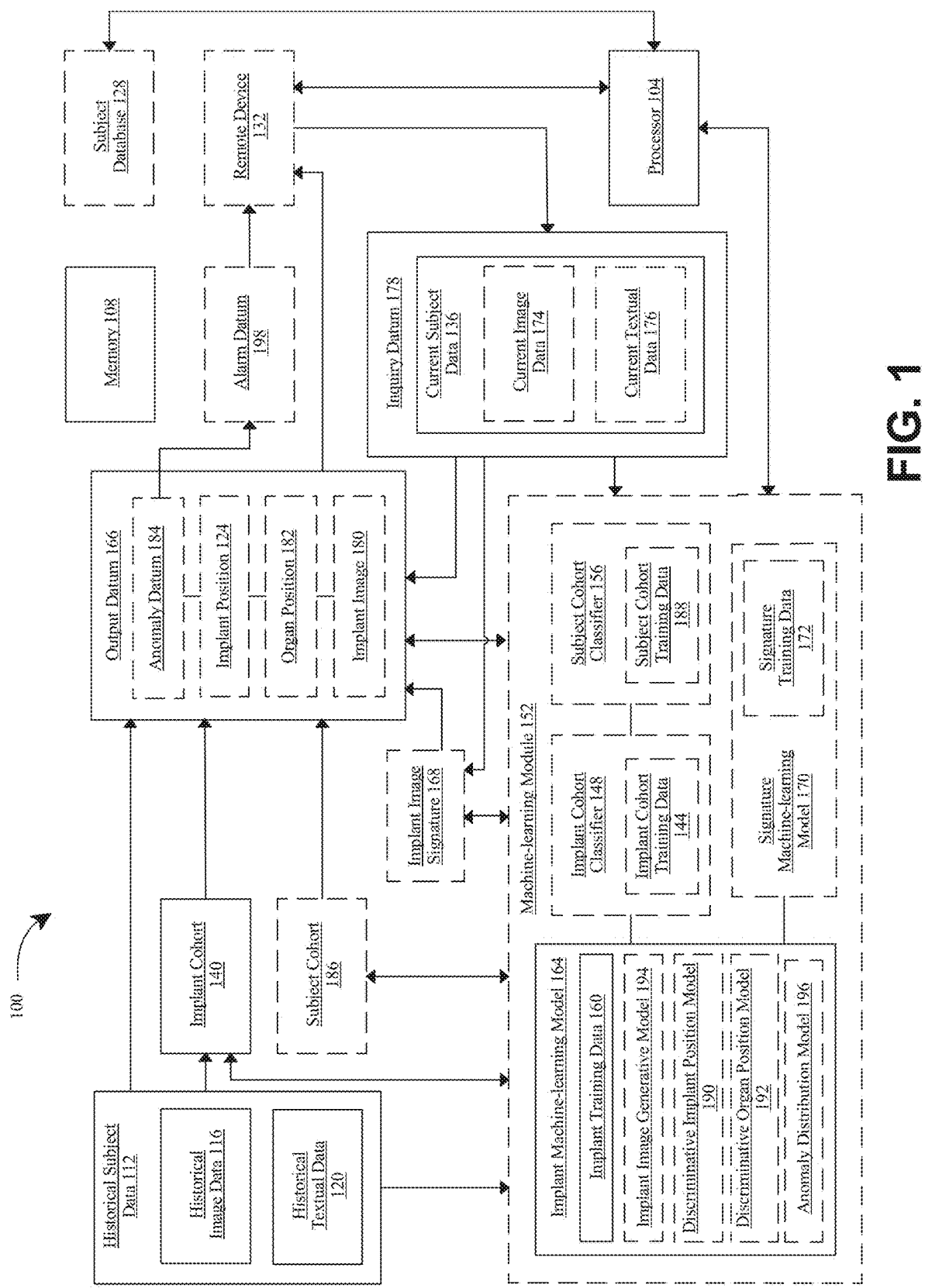
FIG. 1 illustrates a block diagram of an exemplary apparatus for leveraging a repository of images containing implant devices in a human body.

Referring now to FIG. 1, an exemplary embodiment of an apparatus 100 for leveraging a repository of images containing implant devices in a human body is illustrated. Apparatus 100 includes at least a processor 104. Processor 104 may include, without limitation, any processor described in this disclosure. Processor 104 may be included in a computing device. Processor 104 may include any computing device as described in this disclosure, including without limitation a microcontroller, microprocessor, digital signal processor (DSP) and/or system on a chip (SoC) as described in this disclosure. Processor 104 may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented, as a non-limiting example, using a "shared nothing" architecture.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, apparatus 100 includes a memory 108 communicatively connected to processor 104. For the purposes of this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, memory 108 contains instructions configuring processor 104 to receive a plurality of sets of historical subject data 112. For the purposes of this disclosure, a plurality of sets of "historical subject data" is data related to a collection of medical records and health-related information documenting medical history and past health interactions of subjects over time in the past. For the purposes of this disclosure, "subject data" is any data related to a subject. For the purposes of this disclosure, a "subject" is an individual who receives medical care, treatment, or consultation from a user. As a non-limiting example, subject may include a patient in various healthcare settings, including hospitals, clinics, outpatient facilities, long-term care centers, and home healthcare environments. Patients may be of any age, gender, or demographic background, and their interactions with the healthcare system can range from short-term acute care to long-term ongoing treatment and monitoring. For the purposes of this disclosure, a "user" is an individual or organization that provides healthcare services to subjects. As a non-limiting example, user may include doctors, nurses, therapists, radiologists, or other medical practitioners.

With continued reference to FIG. 1, a plurality of sets of historical subject data 112 includes historical image data 116 and historical textual data 120 related to an implant device implanted in a subject's body. For the purposes of this disclosure, an "implant device" is a medical device designed and intended for placement inside of the human body. In a non-limiting example, implant device may be engineered to either replace a missing biological structure, such as joint replacements (e.g., hip or knee implants), dental implants for tooth restoration, or cardiac pacemakers for regulating heart rhythms; to provide structural support to biological tissues or structures, such as orthopedic implants like plates, screws, or rods used in fracture fixation or spinal stabilization; or to enhance bodily functions by improving physiological processes, such as cochlear implants for hearing enhancement, neurostimulators for pain management, or implantable drug delivery systems. Additionally, implant devices may serve diagnostic purposes, such as implantable cardiac monitors or glucose sensors for continuous monitoring in diabetes management. In a non-limiting example, implant device may a left atrial appendage occlusion device (LAAO), implantable cardioverter defibrillator, pacemaker, continuous glucose monitor (CGM), insulin pump, coronary stent, ventricular assist device (VAD), prosthetic heart valve, cochlear implant, spinal cord stimulator, deep brain stimulator, infusion pump, dialysis machine, intraocular lens, endoscopic stapler, surgical robot, transcatheter heart valve, infusion catheter, balloon angioplasty catheter, external defibrillator, pulse oximeter, electrosurgical unit, laparoscope, hemodialysis catheter, bone growth stimulator, neuroprosthesis, artificial pancreas, gastric band, hip replacement implant, knee replacement implant, external fixator, bone cement, dental implant, hearing aid, sleep apnea device, continuous positive airway pressure (CPAP) machine, negative pressure wound therapy device, automated external defibrillator (AED), electrocautery device, inhaler, nebulizer, oxygen concentrator, portable ventilator, diagnostic ultrasound machine, and the like.

With continued reference to FIG. 1, for the purposes of this disclosure, "historical image data" is image data that is related to subjects that were under medical care or observation by users in the past. For the purposes of this disclosure, "image data" is digital information that represents visual images. In some embodiments, image data may include a digital representations of anatomical structures, medical conditions, or implant devices implanted in a human body. As a non-limiting example, historical image data 116 may include an image of anatomical structures and implanted device. In some embodiments, image data may be captured through imaging modalities like X-ray radiography, computed tomography (CT), magnetic resonance imaging (MRI), ultrasound, or other specialized imaging techniques. In a non-limiting example, image data may include visual information depicting internal body structures, including bones, tissues, organs, and the precise positioning and integration of medical implants, prosthetics, or devices within the patient's anatomy. In some embodiments, image data may be stored in digital formats, allowing for detailed examination, analysis, and interpretation by healthcare professionals to assess medical conditions, monitor treatment progress, plan surgical interventions, and ensure the optimal placement, function, and compatibility of implanted devices. In some embodiments, image data may be in printed formats.

With continued reference to FIG. 1, for the purposes of this disclosure, "textual data" is information that is represented in the form of text. As a non-limiting example, textual data may include documentation written by users related to the implantation of an implant into a subject's body. For the purposes of this disclosure, "historical textual data" is textual data that is related to subjects that were under medical care or observation by users in the past. As a non-limiting example, textual data may include clinical notes from users, including notes from doctor visits, hospital admissions, discharge summaries, consultation reports, surgery reports, and the like. As another non-limiting example, textual data may include implant placement details (e.g., implant position 124 described in detail below), descriptions of the surgical approach, any complications encountered, the outcomes of the procedure, intra-operative findings, and post-operative observations. As another non-limiting example, textual data may include information related to an implant device placed in a subject's body. For example, and without limitation, textual data may include manufacturer, the type and specifications of the implanted device, including serial numbers or identifiers, and the like.

With continued reference to FIG. 1, in some embodiments, historical subject data 112 may include detailed medical history of a subject, including past illnesses, surgeries, chronic conditions, and genetic predispositions, along with diagnostic records including results from blood tests, and other diagnostic procedures. It also includes treatment records detailing past and ongoing treatments, prescribed medications, dosages, therapies received, and patient responses to these treatments. As another non-limiting example, historical subject data 112 may include lifestyle and behavioral information, such as diet, exercise habits, smoking, alcohol consumption, and other behaviors impacting health. As another non-limiting example, historical subject data 112 may include family medical history providing insights into genetic or hereditary conditions. As another non-limiting example, historical subject data 112 may include social and demographic information, such as age, gender, ethnicity, and occupation, which influence health.

With continued reference to FIG. 1, in some embodiments, processor 104 may receive historical subject data 112 from electronic health record (EHR). For the purposes of this disclosure, an "electronic health record" is the systematized collection of patient and population electronically stored health information in a digital format. In some embodiments, processor 104 may receive historical subject data 112 using an application programming interface (API). As used in the current disclosure, an "application programming interface" is a software interface for two or more computer programs to communicate with each other. As a non-limiting example, API may include EHR APIs, telemedicine APIs, and the like. An application programming interface may be a type of software interface, offering a service to other pieces of software. In contrast to a user interface, which connects a computer to a person, an application programming interface may connect computers or pieces of software to each other. An API may not be intended to be used directly by a person (e.g., user) other than a computer programmer who is incorporating it into the software. An API may be made up of different parts which act as tools or services that are available to the programmer. A program or a programmer that uses one of these parts is said to call that portion of the API. The calls that make up the API are also known as subroutines, methods, requests, or endpoints. An API specification may define these calls, meaning that it explains how to use or implement them. One purpose of API may be to hide the internal details of how a system works, exposing only those parts a programmer will find useful and keeping them consistent even if the internal details later change. An API may be custom-built for a particular pair of systems, or it may be a shared standard allowing interoperability among many systems. The term API may be often used to refer to web APIs, which allow communication between computers that are joined by the internet. API may be configured to query for web applications in order to retrieve historical subject data 112 to another web application, database (e.g., subject database 128), medical center patient portal, and the like. An API may be further configured to filter through web applications according to a filter criterion. In this disclosure, "filter criteria" are conditions the web applications must fulfill in order to qualify for API. Web applications may be filtered based on these filter criteria. Filter criteria may include, without limitation, types of medical facilities, location of the medical facility, and the like.

With continued reference to FIG. 1, in some embodiments, processor 104 may receive historical subject data 112 from remote device 132. For the purposes of this disclosure, a "remote device" is a computer device separate and distinct from apparatus 100. As a non-limiting example, remote device 132 may include a laptop, desktop, tablet, mobile phone, smart phone, smart watch, kiosk, smart headset, or things of the like. As a non-limiting example, user may include a physician, clinician, nurses, medical professionals, hospitals, medical organization, and the like. In some embodiments, remote device 132 may include an interface configured to receive inputs from user. In some embodiments, user may manually input any data into apparatus 100 using remote device 132. In some embodiments, user may have a capability to process, store or transmit any information independently.

With continued reference to FIG. 1, in some embodiments, apparatus 100 may include a subject database 128. As used in this disclosure, "subject database" is a data store configured to store data associated with subject data. As a non-limiting example, subject database 128 may store historical subject data 112, current subject data 136, information related to patients or users, and the like. In one or more embodiments, subject database 128 may include inputted or calculated information and datum related to historical subject data 112 or current subject data 136. In some embodiments, a datum history may be stored in subject database 128. As a non-limiting example, the datum history may include real-time and/or previous inputted data related to historical subject data 112 or current subject data 136. As a non-limiting example, subject database 128 may include instructions from a user, who may be an expert user, a past user in embodiments disclosed herein, or the like, where the instructions may include examples of the data related to historical subject data 112 or current subject data 136.

With continued reference to FIG. 1, in some embodiments, processor 104 may be communicatively connected with subject database 128. For example, and without limitation, in some cases, subject database 128 may be local to processor 104. In another example, and without limitation, subject database 128 may be remote to processor 104 and communicative with processor 104 by way of one or more networks. The network may include, but is not limited to, a cloud network, a mesh network, and the like. By way of example, a "cloud-based" system can refer to a system which includes software and/or data which is stored, managed, and/or processed on a network of remote servers hosted in the "cloud," e.g., via the Internet, rather than on local severs or personal computers. A "mesh network" as used in this disclosure is a local network topology in which the infrastructure processor 104 connect directly, dynamically, and non-hierarchically to as many other computing devices as possible. A "network topology" as used in this disclosure is an arrangement of elements of a communication network. The network may use an immutable sequential listing to securely store subject database 128. An "immutable sequential listing," as used in this disclosure, is a data structure that places data entries in a fixed sequential arrangement, such as a temporal sequence of entries and/or blocks thereof, where the sequential arrangement, once established, cannot be altered or reordered. An immutable sequential listing may be, include and/or implement an immutable ledger, where data entries that have been posted to the immutable sequential listing cannot be altered.

With continued reference to FIG. 1, in some embodiments, subject database 128 may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described in this disclosure. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

With continued reference to FIG. 1, memory 108 contains instructions configuring processor 104 to classify a plurality of sets of historical subject data 112 into one or more implant cohorts 140. For the purposes of this disclosure, an "implant cohort" is a defined group of one or more implant devices. As a non-limiting example, implant cohort 140 may include a specifically defined group of implant devices related to a particular manufacturer, manufactured date of implant device, type of implant devices, and the like. In some embodiments, user may manually classify historical subject data 112 into one or more implant cohorts 140. In some embodiments, processor 104 may retrieve one or more implant cohorts 140 from subject database 128.

With continued reference to FIG. 1, in some embodiments, processor 104 may be configured to generate implant cohort training data 144. For the purposes of this disclosure, "implant cohort training data" is data containing correlations that a machine-learning process may use to model relationships between subject data and implant cohorts. In a non-limiting example, implant cohort training data 144 may include correlations between exemplary subject data and exemplary implant cohorts. For example, and without limitation, historical textual data 120 of historical subject data 112 may include a name of a manufacturer of an implant device that is implanted in a patient and the historical subject data 112 may be classified to an implant cohort related to the specific manufacturer of implant devices. For example, and without limitation, historical image data 116 of historical subject data 112 may include an image of a specific type of implant device that is implanted in a patient and the historical subject data 112 may be classified to an implant cohort related to the specific type of implant devices. As a non-limiting example, exemplary subject data may include exemplary historical subject data and/or exemplary current subject data. In this disclosure, subject data disclosed herein may be consistent with historical subject data 112 and/or current subject data 136. In some embodiments, implant cohort training data 144 may be stored in subject database 128. In some embodiments, implant cohort training data 144 may be received from one or more users, subject database 128, external computing devices, and/or previous iterations of processing. As a non-limiting example, implant cohort training data 144 may include instructions from a user, who may be an expert user, a past user in embodiments disclosed herein, or the like, which may be stored in memory and/or stored in subject database 128, where the instructions may include labeling of training examples. In some embodiments, implant cohort training data 144 may be updated iteratively on a feedback loop. As a non-limiting example, processor 104 may update implant cohort training data 144 iteratively through a feedback loop as a function of historical subject data 112, implant cohorts 140, or the like. In some embodiments, processor 104 may be configured to generate an implant cohort classifier 148 of a machine-learning module 152. For the purposes of this disclosure, an "implant cohort classifier" is a machine-learning model that sorts subject data into categories or bins of data, outputting one or more implant cohorts associated therewith. In a non-limiting example, generating implant cohort classifier 148 may include training, retraining, or fine-tuning implant cohort classifier 148 using implant cohort training data 144 or updated implant cohort training data 144. In some embodiments, processor 104 may be configured to classify historical subject data 112 into one or more implant cohorts 140 using implant cohort classifier 148 (i.e. trained or updated implant cohort classifier 148). In some embodiments, generating training data and training machine-learning models may be simultaneous.

With continued reference to FIG. 1, processor 104 may be configured to generate a classifier (such as but not limited to implant cohort classifier 148, subject cohort classifier 156, and the like) using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A)\ P(A)\div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Processor 104 may then calculate a likelihood table by calculating probabilities of different data entries and classification labels. Processor 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, processor 104 may be configured to generate classifier (such as but not limited to implant cohort classifier 148, subject cohort classifier 156, and the like) using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database 128, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With continued reference to FIG. 1, memory 108 contains instructions configuring processor 104 to generate implant training data 160 using a plurality of sets of historical subject data 112 in one or more implant cohorts 140 and train an implant machine-learning model 164 using the implant training data 160. For the purposes of this disclosure, "implant training data" is data containing correlations that a machine-learning process may use to model relationships between image data and textual data of subject data. In a non-limiting example, during the model training phase, historical image data 116 and historical textual data 120 of historical subject data 112 in implant training data 160 may be utilized to teach implant machine-learning model 164 to discern patterns and features indicative of output datums 166. The output datums 166 disclosed herein is further described below. In some embodiments, implant training data 160 may be stored in subject database 128. In some embodiments, implant training data 160 may be received from one or more users, subject database 128, external computing devices, and/or previous iterations of processing. As a non-limiting example, implant training data 160 may include instructions from a user, who may be an expert user, a past user in embodiments disclosed herein, or the like, which may be stored in memory and/or stored in subject database 128, where the instructions may include labeling of training examples. In some embodiments, implant training data 160 may be updated iteratively on a feedback loop. As a non-limiting example, processor 104 may update implant training data 160 iteratively through a feedback loop as a function of historical subject data 112, historical image data 116, historical textual data 120, implant cohorts 140, output of implant cohort classifier 148, implant image signature 168, output of signature machine-learning model 170 trained with signature training data 172, or the like. In some embodiments, processor 104 may be configured to generate an implant machine-learning model 164 of a machine-learning module 152. For the purposes of this disclosure, an "implant machine-learning model" is a machine-learning model that sorts subject data into categories or bins of data, outputting output datums associated therewith. In a non-limiting example, generating implant machine-learning model 164 may include training, retraining, or fine-tuning implant machine-learning model 164 using implant training data 160 or updated implant training data 160. In some embodiments, implant machine-learning model 164 may receive current subject data 136, current image data 174, current textual data 176, inquiry datum 178 or keywords of inquiry datum 178 as an input and may output an output datum 166 (e.g., implant image 180, implant position 124, organ position 182, anomaly datum 184, and the like) related to the input. In a non-limiting example, output of implant machine-learning model 164 (e.g., implant position 124, organ position 182, anomaly datum 184, and the like) may update implant training data 160 so that implant machine-learning model 164 retrained with updated implant training data 160 can generate or determine output datum 166 (e.g., implant image 180, implant position 124, organ position 182, anomaly datum 184, and the like) more accurately or more effectively.

With continued reference to FIG. 1, in some embodiments, implant machine-learning model 164 may include a Contrastive Visual Representation Learning from Text (ConVIRT model) model or ConVIRT model. For the purposes of this disclosure, a "Contrastive Visual Representation Learning from Text model" is a machine learning framework designed to enhance visual representation learning by leveraging textual information through a contrastive learning approach. For the purposes of this disclosure, a "contrastive learning" is a self-supervised learning approach that aims to learn effective representations by distinguishing between similar (positive) and dissimilar (negative) pairs of data points. In some embodiments, implant machine-learning model 164 or machine-learning module 152 may include ConVIRT model configured to learn visual representations by exploiting naturally occurring pairing of images (e.g., image data [e.g., historical image data 116 and current image data 174]) and textual data (e.g., historical textual data 120 and current textual data 176]). ConVIRT model may be configured to extract meaningful representations from unlabeled data by mapping similar instances close together in a latent space while pushing apart dissimilar instances. As a non-limiting example, ConVIRT model may be configured to learn visual representations by exploiting pairing of subject data (e.g., historical subject data 112 and current subject data 136) and textual outputs (e.g., output datum 166). In some embodiments, ConVIRT model may generate image—text pairs, which may be received as input to large language model (LLM). Additional details of ConVIRT model are described with respect to FIG. 7. A person of ordinary skill in the art, upon reviewing the entirety of this disclosure, will be able to recognize suitable means to implement ConVIRT model and its related aspects for apparatus 100.

With continued reference to FIG. 1, memory 108 contains instructions configuring processor 104 to receive an inquiry datum 178 from a user. For the purposes of this disclosure, an "inquiry datum" is a query or requisition made to retrieve data related to a subject. As a non-limiting example, inquiry datum 178 may include a user's request for output datums 166; for instance, implant image 180, implant position 124, organ position 182, anomaly datum 184, and the like. The output datums 166 disclosed herein are described in detail below. As another non-limiting example, inquiry datum 178 may pertain to decisions made by implant machine-learning model 164 based on current subject data 136 (e.g., current image data 174, current textual data 176, and the like); for instance requests for diagnostic reports, predictive analytics, treatment recommendations generated by implant machine-learning model 164, probability scores for specific diagnoses, segmentation maps highlighting areas of concern, or risk assessments associated with disease progression. Such requests may leverage the model's computational capabilities to augment clinical expertise, providing quantitative insights and evidence-based recommendations to support clinical reasoning and patient management strategies. In some embodiments, processor 104 may query subject database 128 or historical subject data 112 in implant training data 160 using inquiry datum 178 or keywords of inquiry datum 178 to retrieve or access to data that is relevant to inquiry datum 178.

With continued reference to FIG. 1, in some embodiments, user may manipulate user interface or graphical user interface (GUI) to input inquiry datum 178. The user interface disclosed herein is further described below. In a non-limiting example, user may type inquiry datum 178 into remote device 132; for instance, 'what is the position of the organ,' 'give me an image of this patient with an implant device from a manufacturer A,' and the like. In another non-limiting example, user may click an interface element in GUI of remote device 132. In another non-limiting example, user may input inquiry datum 178 through a chatbot system. For the purposes of this disclosure, "chatbot" is an artificial intelligence (AI) program designed to simulate human conversation or interaction through text, voice-based or image-based communication. The chatbot system is further described in detail with respect to FIG. 3. In some embodiments, processor 104 may retrieve inquiry datum 178 from subject database 128.

With continued reference to FIG. 1, in some embodiments, processor 104 may analyze inquiry datum 178 using a language processing module to determine at least a keyword and processor 104 may generate output datum 166 as a function of the at least a keyword of inquiry datum 178. In some embodiments, processor 104 may use a language processing module to find a keyword. The language processing module may be configured to extract one or more words from inquiry datum 178. One or more words may include, without limitation, strings of one or more characters, including without limitation any sequence or sequences of letters, numbers, punctuation, diacritic marks, medical symbols or abbreviations, chemical symbols and formulas, spaces, whitespace, and other symbols, including any symbols usable as textual data. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

With continued reference to FIG. 1, language processing module may operate to produce a language processing model. Language processing model may include a program automatically generated by processor 104 and/or language processing module to produce associations between one or more words extracted from at least a document and detect associations, including without limitation mathematical associations, between such words. Associations between language elements, where language elements include for purposes herein extracted words, relationships of such categories to other such term may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of semantic meaning. As a further example, statistical correlations and/or mathematical associations may include probabilistic formulas or relationships indicating a positive and/or negative association between at least an extracted word and/or a given semantic meaning; positive or negative indication may include an indication that a given document is or is not indicating a category semantic meaning. Whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at computing device, or the like.

With continued reference to FIG. 1, language processing module may generate the language processing model by any suitable method, including without limitation a natural language processing classification algorithm; language processing model may include a natural language process classification model that enumerates and/or derives statistical relationships between input terms and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs, as used herein, are statistical models with inference algorithms that that may be applied to the models. In such models, a hidden state to be estimated may include an association between an extracted words, phrases, and/or other semantic units. There may be a finite number of categories to which an extracted word may pertain; an HMM inference algorithm, such as the forward-backward algorithm or the Viterbi algorithm, may be used to estimate the most likely discrete state given a word or sequence of words. Language processing module may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

With continued reference to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element.

Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

With continued reference to FIG. 1, language processing module may use a corpus of documents to generate associations between language elements in a language processing module may then use such associations to analyze words extracted from one or more documents and determine that the one or more documents indicate significance of a category. In an embodiment, language module and/or processor 104 may perform this analysis using a selected set of significant documents, such as documents identified by one or more experts as representing good information; experts may identify or enter such documents via graphical user interface or may communicate identities of significant documents according to any other suitable method of electronic communication, or by providing such identity to other persons who may enter such identifications into processor 104. Documents may be entered into a computing device by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, processor 104 may automatically obtain the document using such an identifier, for instance by submitting a request to a database or compendium of documents such as JSTOR as provided by Ithaka Harbors, Inc. of New York.

With continued reference to FIG. 1, inquiry datum 178 includes current subject data 136. For the purposes of this disclosure, "current subject data" is data related to a collection of medical records and health-related information documenting medical information and health interactions of a subject who is presently under medical care or observation by a user. In some embodiments, current subject data 136 may be consistent with historical subject data 112 but related to a subject who is presently under medical care or observation by a user. In some embodiments, current subject data 136 may include current image data 174 and/or current textual data 176. For the purposes of this disclosure, "current image data" is image data that is related to a subject who is presently under medical care or observation by a user. As a non-limiting example, current image data 174 may include an image of anatomical structures of a subject who is presently under observation by a user and considering to get an implant device. As another non-limiting example, current image data may include an image of anatomical structures and an implant device attached on the anatomical structures. For the purposes of this disclosure, "current textual data" is textual data that is related to a subject who is presently under medical care or observation by a user. As a non-limiting example, current textual data 176 may include clinical notes by a user related to a subject's current medical condition, lab reports, and the like. In some embodiments, current textual data 176 may be analyzed using a language processing module or large language model.

With continued reference to FIG. 1, in some embodiments, processor 104 may classify current subject data 136 or historical subject data 112 into one or more subject cohorts 186. For the purposes of this disclosure, a "subject cohort" is a specifically defined group of subjects. As a non-limiting example, subject cohort 186 may include a specifically defined group of subjects related to their age, gender, medical history, existing medical condition, weight, surgical experience, and the like. In some embodiments, user may manually classify current subject data 136 into one or more subject cohorts 186. In some embodiments, processor 104 may retrieve one or more subject cohorts 186 from subject database 128.

With continued reference to FIG. 1, in some embodiments, processor 104 may be configured to generate subject cohort training data 188. For the purposes of this disclosure, "subject cohort training data" is data containing correlations that a machine-learning process may use to model relationships between subject data and subject cohorts. In a non-limiting example, subject cohort training data 188 may include correlations between exemplary subject data and exemplary subject cohorts. As a non-limiting example, exemplary subject data may include exemplary historical subject data and/or exemplary current subject data. In some embodiments, subject cohort training data 188 may be stored in subject database 128. In some embodiments, subject cohort training data 188 may be received from one or more users, subject database 128, external computing devices, and/or previous iterations of processing. As a non-limiting example, subject cohort training data 188 may include instructions from a user, who may be an expert user, a past user in embodiments disclosed herein, or the like, which may be stored in memory and/or stored in subject database 128, where the instructions may include labeling of training examples. In some embodiments, subject cohort training data 188 may be updated iteratively on a feedback loop. As a non-limiting example, processor 104 may update subject cohort training data 188 iteratively through a feedback loop as a function of historical subject data 112, implant cohorts 140, output of implant cohort classifier 148, current subject data 136, subject cohorts 186, or the like. In some embodiments, processor 104 may be configured to generate a subject cohort classifier 156 of a machine-learning module 152. For the purposes of this disclosure, a "subject cohort classifier" is a machine-learning model that sorts subject data into categories or bins of data, outputting one or more subject cohorts associated therewith. In a non-limiting example, generating subject cohort classifier 156 may include training, retraining, or fine-tuning subject cohort classifier 156 using subject cohort training data 188 or updated subject cohort training data 188. In some embodiments, processor 104 may be configured to classify historical subject data 112 into one or more subject cohorts 186 using subject cohort classifier 156 (i.e. trained or updated subject cohort classifier 156). In some embodiments, generating training data and training machine-learning models may be simultaneous. In some embodiments, processor 104 may update implant training data 160 as a function of output of subject cohort classifier 156 or subject cohorts 186 and generate output datum 166 using implant machine-learning model 164 retrained with the updated implant training data 160.

With continued reference to FIG. 1, processor 104 is configured to generate an output datum 166 using implant machine-learning model 164. For the purposes of this disclosure, an "output datum" is information that is produced by an implant machine-learning model after processing current subject data. Output datum 166 is related to a position of an implant device within a subject's body. In some embodiments, output datum 166 may include a variety of detailed analytical results that contribute to the overall clinical interpretation and decision-making process. As a non-limiting example, output datum 166 may include an implant image 180, implant position 124, organ position 182, anomaly datum 184, and the like. In some embodiments, user may manually input output datum 166. In some embodiments, processor 104 may generate output datum 166 from subject database 128. In some embodiments, processor 104 may generate output datum 166 through the use of machine-learning module 152 that includes implant machine-learning model 164.

With continued reference to FIG. 1, in some embodiments, generating output datum 166 may include generating an implant image signature 168 and generating output datum 166 as a function of implant image signature 168. For the purposes of this disclosure, an "implant image signature" is a visual feature or characteristic of an implant device. As a non-limiting example, implant image signature may include shape, size, texture, and specific geometric patterns of implant device. In a non-limiting example, implant devices that have difference functions may have their own unique implant image signature 168. For example, and without limitation, hip implant may have different size, shape, and the like compared to heart valve implant. In another non-limiting example, implant devices that have a same function but different manufacturers may have their own unique implant image signature 168. For example, and without limitation, implant device for LAAO manufactured from a manufacturer A may have different size, shape, and the like compared to implant device for LAAO manufactured from a manufacturer B. In some embodiments, user may manually input implant image signature 168. In some embodiments, processor 104 may retrieve implant image signature 168 from subject database 128.

With continued reference to FIG. 1, in some embodiments, processor 104 may be configured to generate signature training data 172. In a non-limiting example, signature training data 172 may include correlations between exemplary current subject data or current image data correlated to exemplary implant image signatures. In some embodiments, signature training data 172 may be stored in subject database 128. In some embodiments, signature training data 172 may be received from one or more users, subject database 128, external computing devices, and/or previous iterations of processing. As a non-limiting example, signature training data 172 may include instructions from a user, who may be an expert user, a past user in embodiments disclosed herein, or the like, which may be stored in memory and/or stored in subject database 128, where the instructions may include labeling of training examples. In some embodiments, signature training data 172 may be updated iteratively on a feedback loop. As a non-limiting example, processor 104 may update signature training data 172 iteratively through a feedback loop as a function of an output of subject cohort classifier 156, implant cohort classifier 148, and the like. In some embodiments, processor 104 may be configured to generate signature machine-learning model of machine-learning module 152. In a non-limiting example, generating signature machine-learning model may include training, retraining, or fine-tuning signature machine-learning model using signature training data 172 or updated signature training data 172. In some embodiments, processor 104 may be configured to determine implant image signature 168 using signature machine-learning model 170 (i.e. trained or updated signature machine-learning model 170). In some embodiments, generating training data and training machine-learning models may be simultaneous.

With continued reference to FIG. 1, for the purposes of this disclosure, an "implant position" is a spatial location or orientation of an implant device that has been surgically implanted within a human body. In some embodiments, implant position 124 may be determined by a discriminative implant position model 190 of implant position implant machine-learning model 164 by analyzing current image data 174 and/or current subject data 136 that depicts subject's organ and implant device within the subject's body. The discriminative implant position model 190 is described in detail below. In some embodiments, implant position 124 may be defined within a three-dimensional coordinate system including x, y, and z axes that correspond to the anatomical planes (axial, sagittal, and coronal). In some embodiments, implant position 124 may detect exact location of implant device in current image data 174 relative to the surrounding anatomical structures. For instance, the position of a hip prosthesis might be described relative to the acetabulum and femoral shaft. Additionally, in some embodiments, implant position 124 may include the orientation and alignment of the implant, which include the angles and rotational placement within the body. In a non-limiting example, a CT scan image (e.g., current image data 174 or historical image data 116) used to describe the position of a coronary stent may detail its spatial coordinates within the coronary artery, providing information on its exact placement and the degree of arterial patency. For example, a CT scan image describing the position of a spinal implant may include spatial coordinates within coordinate system of the CT scan, such as (x=150, y=250, z=75). Anatomical landmarks may be specified, indicating the implant's position relative to vertebrae, intervertebral discs, and the spinal cord. The orientation and alignment details may provide information on the angles and rotational placement of the implant components. Multiple CT slices may offer comprehensive views from different planes, highlighting the implant's interaction with the vertebral column and surrounding tissues.

With continued reference to FIG. 1, for the purposes of this disclosure, a "discriminative implant position model" is a machine-learning model that is used in a discriminative fashion to determine an implant position. In some embodiments, a discriminative model may include a statistical model designed for classification and regression tasks. Discriminative models may focus on modeling the conditional probability of the labels (e.g., implant position 124) given the input data (e.g., current image data 174 and/or current subject data 136). This targeted approach can allow discriminative models to directly learn the decision boundaries between different classes, making them effective for tasks that involve distinguishing between various categories. Discriminative models can estimate the conditional probability $P(y|x)$, where y represents the label or target variable, and x represents the input features. Discriminative models can bypass the need to model the underlying data distribution, which may lead to more accurate and computationally efficient models.

With continued reference to FIG. 1, in some embodiments, discriminative models can learn decision boundaries. By doing so, these models can classify new instances by understanding the precise separations between different classes. During training, discriminative models can optimize a loss function that measures the discrepancy between the predicted labels and the true labels. For classification tasks, a common loss function is the cross-entropy loss, defined as $L(y, \hat{y}) = -\Sigma_i y_i \log(\hat{y}_i)$, where y is the true label and $\hat{y}$ is the predicted probability. For regression tasks, the mean squared error is often used, given by $$L(y, \hat{y}) = \frac{1}{n}\sum_i (y_i - \hat{y}_i)^2.$$

In some embodiments, optimization techniques such as gradient descent may be employed to minimize these loss functions, ensuring that the model parameters are adjusted to improve performance over time.

With continued reference to FIG. 1, in some embodiments, logistic regression can model the probability that a given instance belongs to a particular class using the logistic function. The logistic regression model can be expressed as $$P(y=1|x) = \frac{1}{1 + \exp(-w^T x - b)},$$

where w is the weight vector, x is the feature vector, and b is the bias term. The model can estimate the parameters w and b by maximizing the likelihood of the observed data. This approach enables logistic regression to effectively classify instances by learning the optimal decision boundary that separates the classes.

With continued reference to FIG. 1, in some embodiments, discriminative implant position model 190 may include Support Vector Machines (SVMs) that find the optimal hyperplane separating different classes in the feature space. SVMs maximize the margin between the nearest data points of different classes, known as support vectors. The optimization problem for SVMs can be formulated as $$\min_{w,b} \frac{1}{2}\|w\|^2 \text{ subject to } y_i(w^T x_i + b) \geq 1$$

for all training samples $(x_i, y_i)$ SVMs can handle both linear and non-linear classification by using kernel functions to transform the feature space, enabling them to capture complex relationships between the features and the labels.

With continued reference to FIG. 1, in some embodiments, discriminative implant position model 190 may include neural networks, including deep learning models, capable of learning complex non-linear relationships between input features and labels. Convolutional Neural Networks (CNNs) and Recurrent Neural Networks (RNNs) are specialized architectures designed for specific tasks. CNNs can be effective for image recognition (e.g., from current image data and historical image data 116) due to their ability to capture spatial hierarchies in the data through convolutional layers. The forward pass of a CNN may involve convolving the input image (e.g., from current image data and historical image data 116) with learned filters (e.g., image training data 160), followed by pooling and non-linear activation functions to generate feature maps. RNNs, on the other hand, can be suited for sequence prediction tasks such as language modeling and speech recognition, as they can capture temporal dependencies in the data by maintaining hidden states that are updated at each time step. The training of neural networks may involve backpropagation, where the gradients of the loss function with respect to the network parameters are computed and used to update the parameters through gradient descent.

With continued reference to FIG. 1, in some embodiments, discriminative implant position model 190 may include Conditional Random Fields (CRFs) used for structured prediction tasks, where the goal is to predict multiple interdependent labels. CRFs may model the conditional probability of the entire label sequence given the input sequence, making them suitable for tasks like sequence labeling and segmentation. The conditional probability of a label sequence y given an input sequence x is defined as $$P(y|x) = \frac{1}{z(x)}\exp\left(\sum_i w^T f(y_i, x, i)\right),$$

where f are feature functions, w are the model parameters, and Z(x) is the normalization factor. Training CRFs may involve maximizing the conditional likelihood of the training data (e.g., implant training data 160), which can be done using gradient-based optimization methods.

With continued reference to FIG. 1, for the purposes of this disclosure, an "organ position" is a spatial location and orientation of an anatomical structure within the body as visualized through current image data of current subject data. In some embodiments, organ position 182 may be determined by a discriminative organ position model 192 of implant machine-learning model 164 by analyzing current subject data 136 and implant position 124. The discriminative organ position model 192 is disclosed in detail below. As a non-limiting example, organ position 182 may include a three-dimensional coordinate system, described in terms of x, y, and z axes corresponding to the anatomical planes of axial, sagittal, and coronal. In some embodiments, organ position 182 may include the organ's position relative to other anatomical landmarks or reference points within the body. For instance, the liver's position might be specified in relation to the ribcage, diaphragm, and vertebral column. In addition to spatial coordinates, in some embodiments, organ position 182 may include the orientation of the organ, including its anatomical alignment and the angles at which it is situated relative to the imaging planes. For example, and without limitation, a CT scan image used to describe the position of the heart may detail its spatial coordinates within the coordinate system of the CT scan, such as (x=100, y=200, z=50). The anatomical landmarks may be described, indicating the heart's position in the mediastinum, anterior to the spine, posterior to the sternum, and flanked by the lungs. The orientation and alignment details may specify that the heart's apex points downward and to the left, with the right atrium and ventricle forming the right border visible in the coronal plane. Multiple CT slices may provide comprehensive views from the top of the heart down to the diaphragm, highlighting different sections like the atria, ventricles, and major vessels.

With continued reference to FIG. 1, for the purposes of this disclosure, a "discriminative organ position model" is a machine-learning model that is used in a discriminative fashion to determine an organ position. In some embodiments, discriminative organ position model 192 may include any discriminative models described in this disclosure. As a non-limiting example, discriminative organ position model 192 may include logistic regression, SVMs, neural networks, CRFs, and the like.

With continued reference to FIG. 1, for the purposes of this disclosure, an "implant image" is an image that shows both the anatomical structures of a subject's body and an implant device that can be implanted in the body. In some embodiments, inquiry datum 178 may include a user's request for an implant image of a specific subject with a specific type of implant device or implant device from a specific manufacturer and processor 104 may generate implant image 180 using an implant image generative model 194 of implant machine-learning model 164 by adding an image of implant device into current image data 174 of current subject data 136 that only depicts a subject's organ. This, in a non-limiting example, may be generated as a function of organ position 182 of current image data 174 by adding an image of implant device with respect to the position of organ in current image data 174.

With continued reference to FIG. 1, for the purposes of this disclosure, a "implant image generative model" is a generative model that generates an implant image. A diffusion model may model and simulate the progressive refinement of image data (e.g., historical image data 116 and current image data 174) through iterative diffusion processes. Diffusion model may capture the transformation of noise into coherent image structures, enabling the generation of high-fidelity synthetic images.

With continued reference to FIG. 1, in some embodiments, diffusion models may operate by iteratively refining an image through a series of steps, starting from pure noise and progressively adding detail until a clear, high-resolution image is formed. This process can be mathematically described using a forward and reverse diffusion process, governed by stochastic differential equations. In the forward diffusion process, noise is gradually added to the image data (e.g., historical image data 116 and current image data 174), transforming an initial image $x_0$ into a series of increasingly noisy images $x_t$ over time t. The process is represented as $x_t = \sqrt{1-\beta_t} x_{t-1} + \sqrt{\beta_t} \epsilon$, where $\beta_t$ is the variance schedule controlling the amount of noise added at each step, and $\epsilon$ is sampled from a standard Gaussian distribution N(0, I).

With continued reference to FIG. 1, in some embodiments, conversely, reverse diffusion process aims to generate a clean image from noise by iteratively denoising the noisy image $X_T$ back to $x_0$. This reverse process is defined by $$x_{t-1} = \frac{1}{\sqrt{1-\beta_t}}(x_t - \sqrt{\beta_t}\, \epsilon_\theta(x_t, t)),$$

where $\epsilon_\theta(x_t, t)$ is a neural network trained to predict the added noise at each step. The training objective for the model can be expressed as a simplified version of the variational lower bound (ELBO): $L(\theta)=E_{t,x_0,\epsilon}[\|\epsilon - \epsilon_\theta(x_t, t)\|^2]$, where $\|\cdot\|^2$ denotes the mean squared error, and the expectation is taken over the time steps t, original images $x_0$, and noise $\epsilon$.

With continued reference to FIG. 1, in some embodiments, diffusion model can be trained on large datasets of images (e.g., historical image data 116 of image training data 160) to learn the underlying distribution of image data, enabling it to generate new images (e.g., implant image 180) that are statistically similar to the training set. The implementation of this model may include initializing with an initial random noise image $X_T \sim N(0, I)$, using a deep neural network $\epsilon_\theta$ (e.g., U-Net) to predict the noise c at each step, and applying the reverse diffusion equation iteratively from t=T to t=1 to generate the image.

With continued reference to FIG. 1, in some embodiments, the mathematical formalism of the forward process is described by the Itô SDE: $dx_t = \beta_t x_t dt + \sqrt{\beta_t} dW_t$, where $W_t$ is a Wiener process. The reverse process is described by the reverse-time SDE:

$$dx_t = \left(\frac{\beta_t}{\sqrt{1-\beta_t}} x_t - \beta_t \epsilon_\theta(x_t, t)\right) dt + \sqrt{\beta_t}\, d\overline{W}_t,$$

where $\overline{W}_t$ is the reverse Wiener process.

With continued reference to FIG. 1, for the purposes of this disclosure, an "anomaly datum" is a datum related to any deviation from the expected or normal anatomical, physiological or structural presentation within current image data. In some embodiments, anomaly datum 184 may be determined using an anomaly distribution model 196 of implant machine-learning model 164 by comparing current image data 174 that depicts a subject's organ and implant device and historical image data 116 that is considered to be expected or normal anatomical, physiological or structural presentation of a subject's organ and implant device and detecting any deviation in current image data 174 compared to historical image data 116. Then, in some embodiments, processor 104 may determine a degree of deviation (e.g., anomaly datum 184) between the current image data 174 and historical image data 116; for instance, how the location of an implant device is compromised or changed from where it should be located at, and the like. In some embodiments, anomaly datum 184 may include structural deformities, misalignments, unexpected placements, pathological changes, and complications associated with the implant device. In a non-limiting example, identifying anomaly datum 184 in medical images may involve a meticulous analysis of the spatial coordinates, orientation, and relationships between the organ tissues and the implant device. For example, a CT scan might reveal an abnormal displacement of a hip prosthesis, indicating potential loosening or migration, which is a significant anomaly requiring immediate clinical attention. As another non-limiting example, anomaly datum 184 may include improper positioning, structural defects, and signs of wear or damage. For instance, a pacemaker lead that has become dislodged from its intended position within the heart chamber may present as an anomaly datum 184. Similarly, for instance, MRI scans may reveal anomaly datum 184 such as fibrotic encapsulation around an implant, indicating a possible adverse tissue reaction that could impede the device's performance.

With continued reference to FIG. 1, for the purposes of this disclosure, an "anomaly distribution model" is a machine-learning model that leverages the probability distribution generated from encoders where the embeddings of the encoder would an anomaly datum. In some embodiments, anomaly distribution model 196 may include encoders, integral components of neural network architectures such as autoencoders or variational autoencoders (VAEs), that can transform input data (e.g., current subject data 136) into a lower-dimensional latent space representation. This latent space, also called embeddings, can encapsulate essential features and structural characteristics of the input data. In some embodiments, encoders may be trained on datasets (e.g., implant training data 160) including medical images or signals that depict the typical placement of implant devices within a body (e.g., historical image data 116). In some embodiments, encoders may learn and model the underlying distribution P(z|x), where z denotes the latent variables (embeddings) and x represents the input data, such as medical images capturing the implant's location (e.g., historical image data 116).

With continued reference to FIG. 1, in some embodiments, embeddings of in-distribution data (e.g., data resembling the training set [e.g., image training data 160]) may cluster around specific regions within the latent space. Conversely, embeddings corresponding to OOD cases, such as implant devices that have shifted due to physiological changes or mechanical factors, may reside in regions of the latent space where the encoder has encountered infrequently during training. Mathematically, the encoder function $z = f_\theta(x)$, parameterized by neural network weights θ, maps the input data x to its corresponding embedding z. This embedding may be modeled as a multivariate Gaussian distribution $P(z) = N(\mu, \Sigma)$, where μ represents the mean and Σ denotes the covariance matrix learned during training. The process can involve optimizing the encoder to accurately capture the distribution of embeddings that best represent the training data.

With continued reference to FIG. 1, to identify potential OOD cases, the system computes the Mahalanobis distance of each embedding zzz from the mean of the learned distribution: $D_M(z) = \sqrt{(z-\mu)^T \Sigma^{-1} (z-\mu)}$. The Mahalanobis distance can serve as a measure of how far an embedding deviates from the typical distribution observed during training. If the computed distance exceeds a predefined threshold, it may signal that the embedding z corresponds to an OOD case, indicating that the implant device has likely moved from its expected position (e.g., anomaly datum 184). This detection mechanism may allow processor 104 to promptly raise alerts (e.g., alarm datum 198).

With continued reference to FIG. 1, for instance, without limitation, consider the scenario of a cardiac implant designed to remain within a specific region of the heart. An encoder (e.g., anomaly distribution model 196), trained on a comprehensive dataset of correctly positioned implants (e.g., implant training data 160), may learn the distribution of embeddings corresponding to this anatomical location. Should the implant shift due to physiological changes or unforeseen circumstances, new imaging data (e.g., current image data 174) processed by the encoder may produce embeddings that deviate from the learned distribution. Detection of such deviations through the Mahalanobis distance metric may enable processor 104 to proactively alert healthcare providers, prompting timely assessments and corrective measures (e.g., alarm datum 198).

With continued reference to FIG. 1, in some embodiments, implant machine-learning model 164 may be designed to generate implant image 180, determine implant position 124, organ position 182, and anomaly datum 184, providing a comprehensive solution for augmenting training data and aiding in diagnostic tasks. In some embodiments, implant machine-learning model 164 may employ a shared encoder-decoder architecture with an additional classification head, optimizing both generative and discriminative functionalities. In some embodiments, the encoder may process current image data 174 of current subject data 136, transforming them into latent representations—compact feature vectors that capture essential data characteristics. The decoder may utilize these latent representations to reconstruct images, fulfilling the generative task to generate implant image 180, while the classification head can predict, detect or determine medical conditions, abnormalities, positions of organs or implant devices (e.g., organ position 182 or implant position 124), addressing the discriminative task. This dual-functionality model (e.g., implant machine-learning model 164) can leverage a combined loss function to ensure balanced optimization for both tasks: the generative loss ($L_{gen}$), measured using Mean Squared Error (MSE) or Binary Cross-Entropy (BCE), may evaluate the fidelity of the reconstructed images (e.g., implant image 180), and the discriminative loss ($L_{dis}$), typically measured using Cross-Entropy Loss, may assess the accuracy of decisions or predictions. The total loss ($L_{total}$) is defined as ($L_{total} = \alpha L_{gen} + \beta L_{disc}$), where α and β are hyperparameters that balance the respective contributions of generative and discriminative tasks. During the forward pass, implant machine-learning model 164 may process current image data 174 through the encoder to obtain a latent vector, which is then used by the decoder to generate implant image 180 and by the classification head to predict or determine implant position 124, organ position 182, anomaly datum 184, or medical condition. The backward pass may involve computing gradients of the total loss with respect to model parameters and updating these parameters using an optimization algorithm to minimize the total loss. This integrated approach may allow implant machine-learning model 164 to perform data augmentation by generating implant image 180, thereby addressing limited data scenarios, and to provide automated diagnostic assistance by accurately determining implant position 124, organ position 182, anomaly datum 184, and the like. The shared feature representations may enhance generalization capabilities of implant machine-learning model 164, improving performance across multiple tasks. The process of training implant machine-learning model 164 and the use of implant machine-learning model 164 may enhance diagnostic processes, aids in medical research, and may improve training efficiency, demonstrating significant potential in the medical imaging domain.

With continued reference to FIG. 1, in some embodiments, implant machine-learning model 164 may incorporate with signature machine-learning model 170. As a non-limiting example, processor 104 may generate output datum 166 (e.g., anomaly datum 184, implant position 124, organ position 182, implant image 180, and the like) as a function of implant image signature 168. In some embodiments, implant image generative model 194, discriminative implant position model 190, discriminative organ position model 192, and anomaly distribution model 196 of implant machine-learning model 164 may use implant image signature 168 to determine output datum 166. In some embodiments, processor 104 may update implant training data 160 as a function of an output of signature machine-learning model 170.

With continued reference to FIG. 1, in some embodiments, processor 104 may be configured to generate an alarm datum 198 as a function of anomaly datum 184. For the purposes of this disclosure, an "alarm datum" is a datum to promptly inform a user related to detected anomaly datum. Upon detecting an anomaly (e.g., anomaly datum 184), processor 104 may generate an alarm datum 198 that can be communicated to a user through various means, including visual, auditory, and electronic notifications. In some embodiments, alarm datum 198 may be customized to include specific details about the anomaly (e.g., anomaly datum 184), such as its location, severity, and potential implications for the patient's health. For example, if a CT scan (e.g., current image data 174) reveals that a hip prosthesis has shifted position (e.g., anomaly datum 184), processor 104 may generate a notification (e.g., alarm datum 198) that includes the exact spatial coordinates of the displacement, the degree of misalignment, and recommendations for further diagnostic tests or immediate clinical actions. In some embodiments, processor 104 may prioritize alarm datum 198 based on the severity of the detected anomaly, ensuring that the most urgent cases receive immediate attention. For example, an alarm datum 198 for a suspected implant infection, which requires rapid intervention, may be flagged as high priority and sent to the attending surgeon and infectious disease specialist without delay. In some embodiments, alarm datum 198 may be configured to provide actionable insights and recommendations based on the detected anomaly. For instance, if processor 104 detects signs of peri-implantitis around a dental implant, it could recommend specific diagnostic tests, such as a microbial culture, and suggest potential treatment options, such as antibiotic therapy or surgical debridement.

With continued reference to FIG. 1, in a non-limiting illustrative example, consider a patient with an implanted cardioverter defibrillator (ICD). During an annual chest X-ray, processor 104 may determine that current image data 174 reveals that the ICD has shifted from its original placement (e.g., output datum 166). This displacement may trigger generation of alarm datum 198 by processor 104, indicating potential risks such as lead displacement or compromised shock delivery. In another non-limiting illustrative example, interventional settings such as surgical procedures or catheterization labs involve immediate, high-stakes scenarios where real-time imaging may be employed to guide the placement and adjustment of implant devices. For example, during the implantation of a spinal cord stimulator intended to alleviate chronic pain, processor 104 may determine intraoperative fluoroscopy (e.g., current image data 174) reveals that one of the electrodes has shifted from its targeted position along the spinal cord (e.g., output datum 166). This real-time positional change may trigger an alarm datum 198 by processor 104, prompting the surgical team to promptly adjust the electrode placement to ensure it lies correctly along the desired nerve pathway. Similarly, in another non-limiting illustrative example, during a percutaneous coronary intervention (PCI) involving the placement of a coronary stent, processor 104 may determine real-time angiography (e.g., current image data 174) indicates that the stent has not fully expanded or has shifted after deployment (e.g., output datum 166).

With continued reference to FIG. 1, in some embodiments, processor 104 may be configured to transmit output datum 166, alarm datum 198, and the like to remote device 132. In some embodiments, processor 104 may be further configured to generate a user interface displaying output datum 166, current subject data 136, and the like on remote device 132. For the purposes of this disclosure, a "user interface" is a means by which a user and a computer system interact; for example through the use of input devices and software. A user interface may include a graphical user interface (GUI), command line interface (CLI), menu-driven user interface, touch user interface, voice user interface (VUI), form-based user interface, any combination thereof and the like. In some embodiments, user interface may operate on and/or be communicatively connected to a decentralized platform, metaverse, and/or a decentralized exchange platform associated with the user. For example, a user may interact with user interface in virtual reality. In some embodiments, a user may interact with the use interface using a computing device distinct from and communicatively connected to at least a processor 104. For example, a smart phone, smart tablet, or laptop operated by a user. In an embodiment, user interface may include a graphical user interface. A "graphical user interface," as used herein, is a graphical form of user interface that allows users to interact with electronic devices. In some embodiments, GUI may include icons, menus, other visual indicators or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pull-down menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. For example, links to decentralized platforms as described in this disclosure may be incorporated using icons. Using an icon may be a fast way to open documents, run programs etc. because clicking on them yields instant access. In some embodiments, GUI may include one or more event handlers. An "event handler" as used in this disclosure is a callback routine that operates asynchronously once an event takes place. Event handlers may include, without limitation, one or more programs to perform one or more actions based on user input, such as generating pop-up windows, submitting forms, changing background colors of a webpage, and the like. Event handlers may be programmed for specific user input, such as, but not limited to, mouse clicks, mouse hovering, touchscreen input, keystrokes, and the like. For instance and without limitation, an event handler may be programmed to generate a pop-up window if a user double clicks on a specific icon. User input may include a manipulation of computer icons, such as, but not limited to, clicking, selecting, dragging and dropping, scrolling, and the like. In some embodiments, user input may include an entry of characters and/or symbols in a user input field. A "user input field" as used in this disclosure is a portion of a graphical user interface configured to receive data from an individual. A user input field may include, but is not limited to, text boxes numerical fields, search fields, filtering fields, and the like. In some embodiments, user input may include touch input. Touch input may include, but is not limited to, single taps, double taps, triple taps, long presses, swiping gestures, and the like. In some embodiments, user input may include inquiry datum 178. One of ordinary skill in the art will appreciate the various ways a user may interact with GUI.

Figure 2:
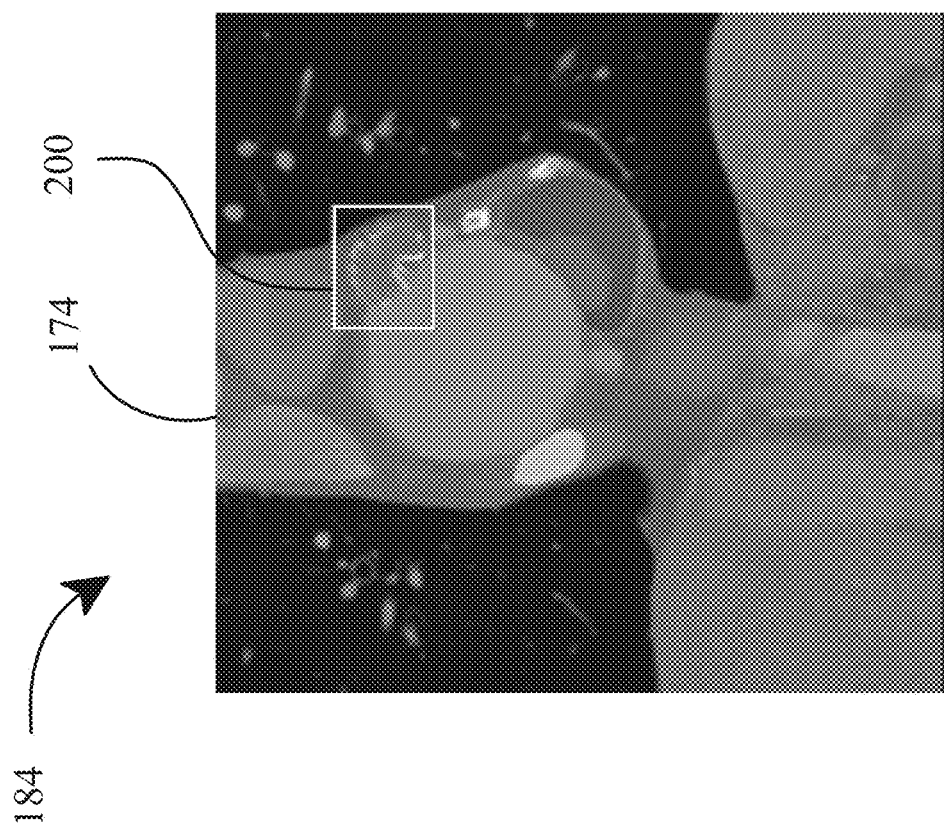
FIG. 2 illustrates an exemplary implant image of an output datum.

Referring now to FIG. 2, an exemplary implant image 180 of an output datum 166 is illustrated. FIG. 2 illustrates an image of a heart (e.g., current image data 174) and image of implant device 200 added to the image of the heart. In some embodiments, implant image 180 may include an image of implant device 200 that a user requested from inquiry datum 178 added to current image data 174 and the image of implant device 200 may be retrieved from historical image data 116.

Figure 3:
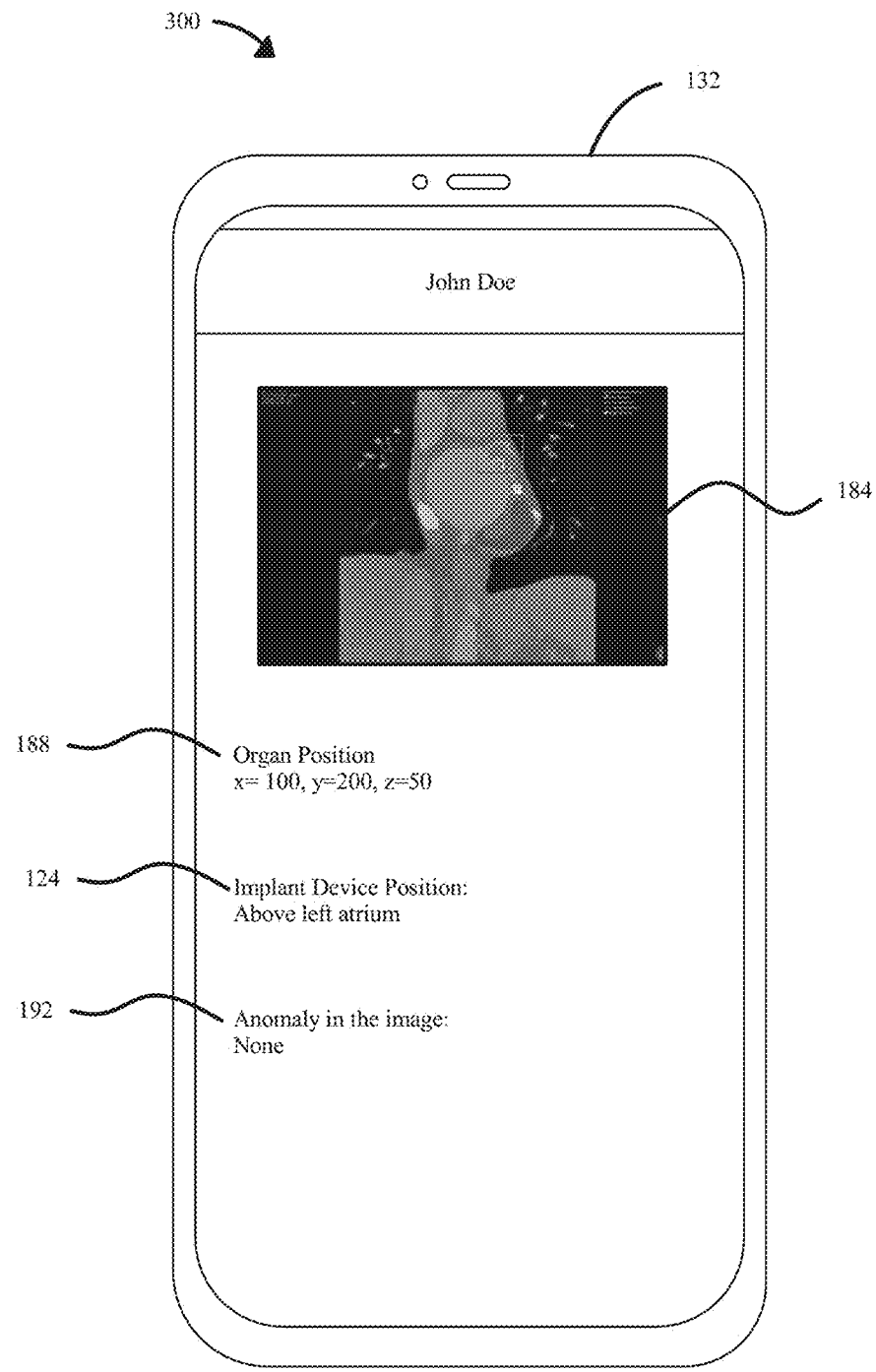
FIG. 3 illustrates an exemplary user interface of a remote device displaying output datums.

Referring now to FIG. 3, an exemplary user interface 300 of a remote device 132 displaying output datums 166 is illustrated. As a non-limiting example, remote device 132 may include a laptop, desktop, tablet, mobile phone, smart phone, smart watch, kiosk, smart headset, or things of the like. In some embodiments, output datum 166 may include a variety of detailed analytical results that contribute to the overall clinical interpretation and decision-making process. As a non-limiting example, output datum 166 may include an implant image 180, implant position 124, organ position 182, anomaly datum 184, and the like.

Figure 4:
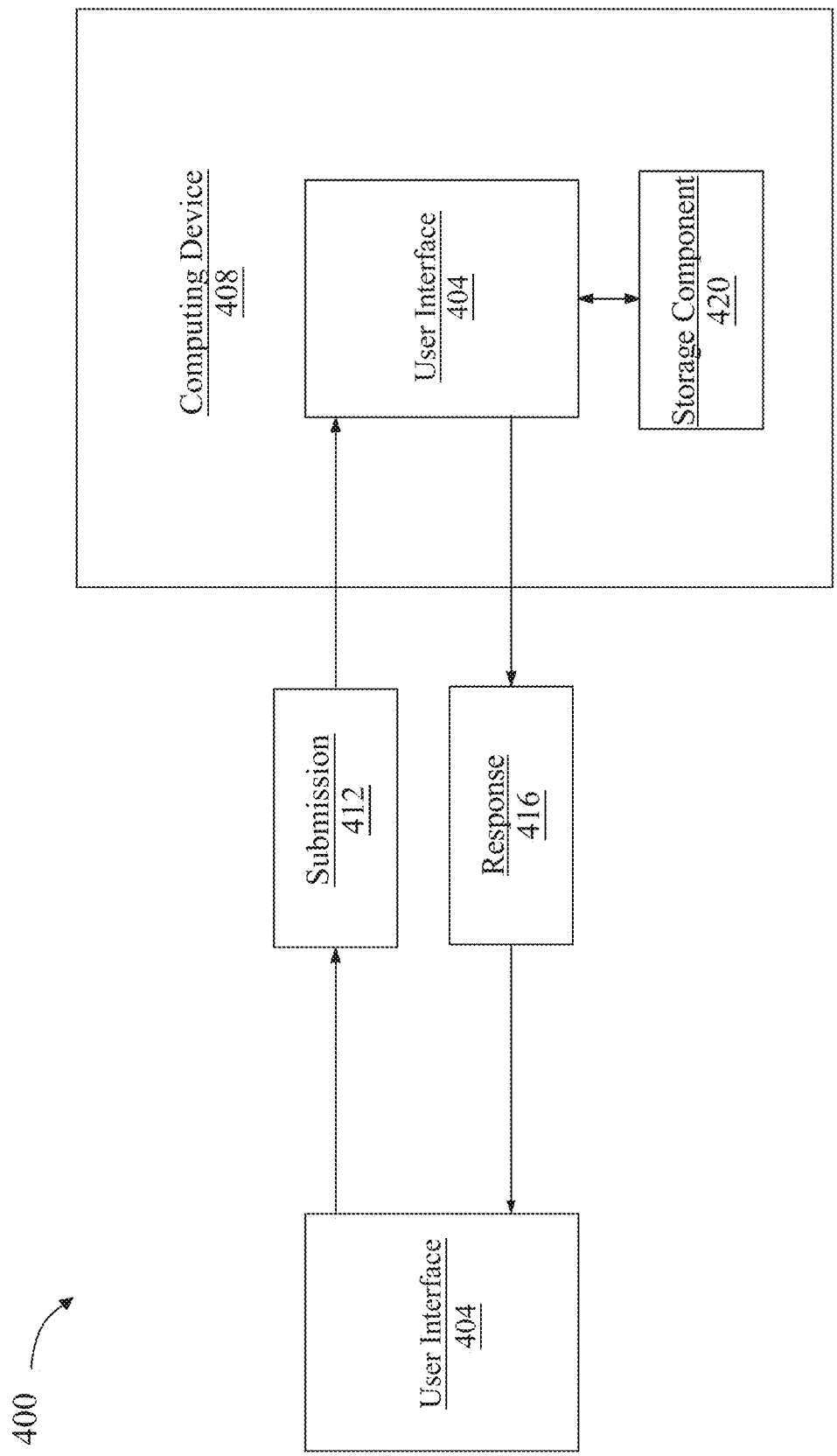
FIG. 4 illustrates a block diagram of an exemplary chatbot system.

Referring now to FIG. 4, a chatbot system 400 is schematically illustrated. According to some embodiments, a user interface 404 may be communicative with a computing device 408 that is configured to operate a chatbot. In some cases, user interface 404 may be local to computing device 408. Alternatively or additionally, in some cases, user interface 404 may remote to computing device 408 and communicative with the computing device 408, by way of one or more networks, such as without limitation the internet. Alternatively or additionally, user interface 404 may communicate with computing device 408 using telephonic devices and networks, such as without limitation fax machines, short message service (SMS), or multimedia message service (MMS). Commonly, user interface 404 communicates with computing device 408 using text-based communication, for example without limitation using a character encoding protocol, such as American Standard for Information Interchange (ASCII). Typically, a user interface 404 conversationally interfaces a chatbot, by way of at least a submission 412, from the user interface 404 to the chatbot, and a response 416, from the chatbot to the user interface 404. In many cases, one or both of submission 412 and response 416 are text-based communication. Alternatively or additionally, in some cases, one or both of submission 412 and response 416 are audio-based communication.

Continuing in reference to FIG. 4, a submission 412 once received by computing device 408 operating a chatbot, may be processed by a processor. In some embodiments, processor processes a submission 412 using one or more of keyword recognition, pattern matching, and natural language processing. In some embodiments, processor employs real-time learning with evolutionary algorithms. In some cases, processor may retrieve a pre-prepared response from at least a storage component 420, based upon submission 412. Alternatively or additionally, in some embodiments, processor communicates a response 416 without first receiving a submission 412, thereby initiating conversation. In some cases, processor communicates an inquiry to user interface 404; and the processor is configured to process an answer to the inquiry in a following submission 412 from the user interface 404. In some cases, an answer to an inquiry present within a submission 412 from a computing device 408 or remote device 132 may be used by computing device 408 as an input to another function.

With continued reference to FIG. 4, a chatbot may be configured to provide a user with a plurality of options as an input into the chatbot. Chatbot entries may include multiple choice, short answer response, true or false responses, and the like. A user may decide on what type of chatbot entries are appropriate. In some embodiments, the chatbot may be configured to allow the user to input a freeform response into the chatbot. The chatbot may then use a decision tree, data base, or other data structure to respond to the users entry into the chatbot as a function of a chatbot input. As used in the current disclosure, "chatbot input" is any response that a user inputs in to a chatbot as a response to a prompt or question.

With continuing reference to FIG. 4, computing device 408 may be configured to the respond to a chatbot input using a decision tree. A "decision tree," as used in this disclosure, is a data structure that represents and combines one or more determinations or other computations based on and/or concerning data provided thereto, as well as earlier such determinations or calculations, as nodes of a tree data structure where inputs of some nodes are connected to outputs of others. Decision tree may have at least a root node, or node that receives data input to the decision tree, corresponding to at least a candidate input into a chatbot. Decision tree has at least a terminal node, which may alternatively or additionally be referred to herein as a "leaf node," corresponding to at least an exit indication; in other words, decision and/or determinations produced by decision tree may be output at the at least a terminal node. Decision tree may include one or more internal nodes, defined as nodes connecting outputs of root nodes to inputs of terminal nodes. Computing device 408 may generate two or more decision trees, which may overlap; for instance, a root node of one tree may connect to and/or receive output from one or more terminal nodes of another tree, intermediate nodes of one tree may be shared with another tree, or the like.

Still referring to FIG. 4, computing device 408 may build decision tree by following relational identification; for example, relational indication may specify that a first rule module receives an input from at least a second rule module and generates an output to at least a third rule module, and so forth, which may indicate to computing device 408 an in which such rule modules will be placed in decision tree. Building decision tree may include recursively performing mapping of execution results output by one tree and/or subtree to root nodes of another tree and/or subtree, for instance by using such execution results as execution parameters of a subtree. In this manner, computing device 408 may generate connections and/or combinations of one or more trees to one another to define overlaps and/or combinations into larger trees and/or combinations thereof. Such connections and/or combinations may be displayed by visual interface to user, for instance in first view, to enable viewing, editing, selection, and/or deletion by user; connections and/or combinations generated thereby may be highlighted, for instance using a different color, a label, and/or other form of emphasis aiding in identification by a user. In some embodiments, subtrees, previously constructed trees, and/or entire data structures may be represented and/or converted to rule modules, with graphical models representing them, and which may then be used in further iterations or steps of generation of decision tree and/or data structure. Alternatively or additionally subtrees, previously constructed trees, and/or entire data structures may be converted to APIs to interface with further iterations or steps of methods as described in this disclosure. As a further example, such subtrees, previously constructed trees, and/or entire data structures may become remote resources to which further iterations or steps of data structures and/or decision trees may transmit data and from which further iterations or steps of generation of data structure receive data, for instance as part of a decision in a given decision tree node.

Continuing to refer to FIG. 4, decision tree may incorporate one or more manually entered or otherwise provided decision criteria. Decision tree may incorporate one or more decision criteria using an application programmer interface (API). Decision tree may establish a link to a remote decision module, device, system, or the like. Decision tree may perform one or more database lookups and/or look-up table lookups. Decision tree may include at least a decision calculation module, which may be imported via an API, by incorporation of a program module in source code, executable, or other form, and/or linked to a given node by establishing a communication interface with one or more exterior processes, programs, systems, remote devices, or the like; for instance, where a user operating system has a previously existent calculation and/or decision engine configured to make a decision corresponding to a given node, for instance and without limitation using one or more elements of domain knowledge, by receiving an input and producing an output representing a decision, a node may be configured to provide data to the input and receive the output representing the decision, based upon which the node may perform its decision.

Figure 5:
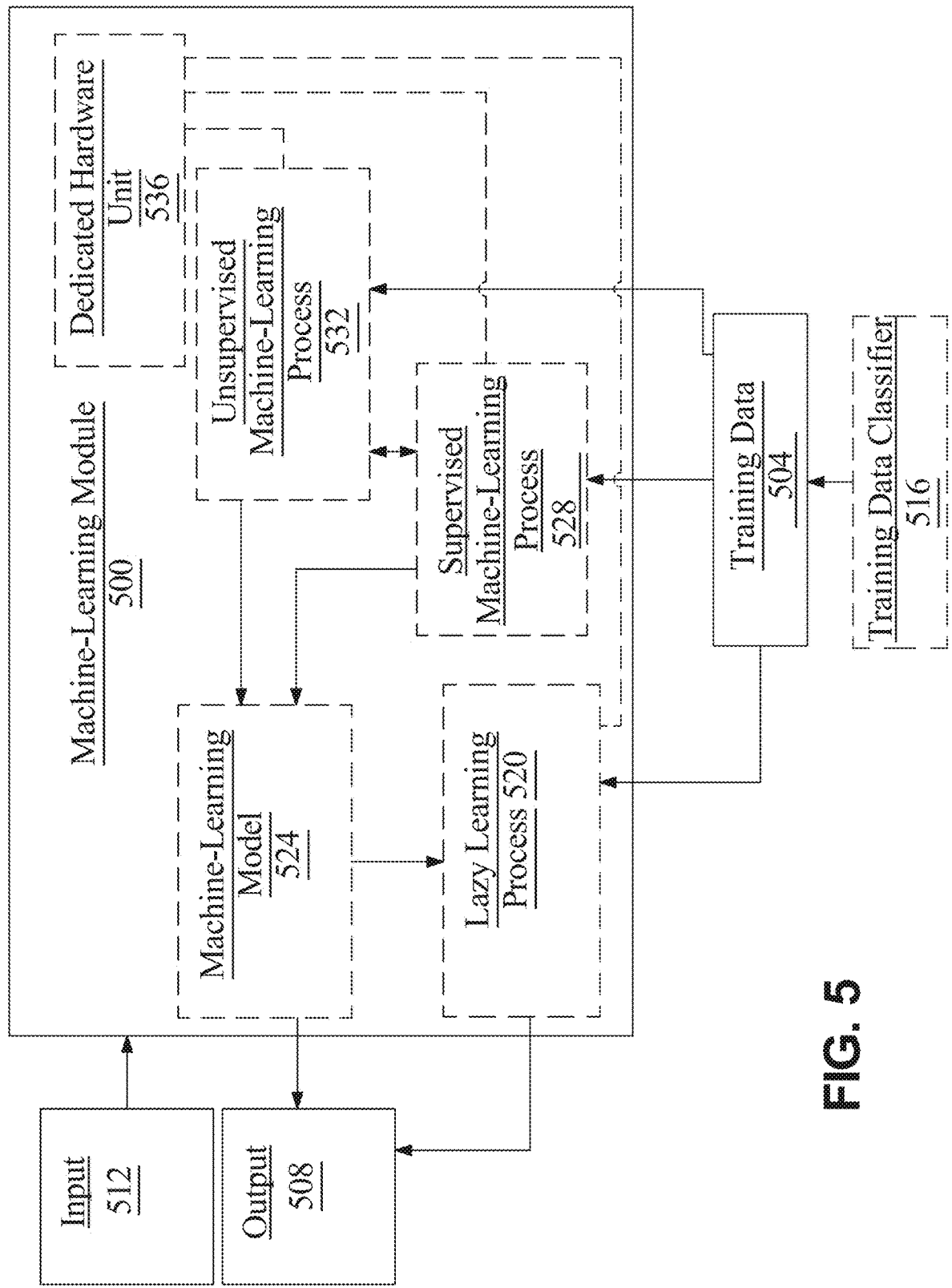
FIG. 5 illustrates a block diagram of an exemplary machine-learning module.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine-learning processes. A "machine-learning process," as used in this disclosure, is a process that automatedly uses training data 504 to generate an algorithm instantiated in hardware or software logic, data structures, and/or functions that will be performed by a computing device/module to produce outputs 508 given data provided as inputs 512; this is in contrast to a non-machine-learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example, input data may include historical subject data 112, implant cohorts 140, inquiry datum 178, output datum 166 and the like. As a non-limiting illustrative example, output data may include historical subject data 112, implant cohorts 140, inquiry datum 178, output datum 166 and the like.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a data structure representing and/or using a mathematical model, neural net, or program generated by a machine-learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to implant cohorts, subject cohorts, and the like. As a non-limiting example, implant cohorts may include a cohort related to different implant types, manufacturers, manufactured dates, and the like. As a non-limiting example, subject cohorts may include a cohort related to different ages, genders, existing conditions, weights, and the like of a subject.

Still referring to FIG. 5, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)÷P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 5, computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 5, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 5, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 5, computer, processor, and/or module may be configured to preprocess training data. "Preprocessing" training data, as used in this disclosure, is transforming training data from raw form to a format that can be used for training a machine-learning model. Preprocessing may include sanitizing, feature selection, feature scaling, data augmentation and the like.

Still referring to FIG. 5, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 5, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 5, computing device, processor, and/or module may be configured to precondition one or more training examples. For instance, and without limitation, where a machine-learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine-learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine-learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 5, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 5, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 5, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max}: X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of a set or subset of values:

$$X_{new} = \frac{X - X_{mean}}{\sigma}.$$

Scaling may be performed using a median value of a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 5, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine-learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528.

At least a supervised machine-learning process 528, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include historical subject data 112, implant cohorts 140, inquiry datum 178, output datum 166 and the like as described above as inputs, historical subject data 112, implant cohorts 140, inquiry datum 178, output datum 166 and the like as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

With further reference to FIG. 5, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 5, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 5, machine-learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 532 may not require a response variable; unsupervised processes 532 may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 5, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 5, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 5, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 5, one or more processes or algorithms described above may be performed by at least a dedicated hardware unit 536. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 536 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 536 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 536 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 6:
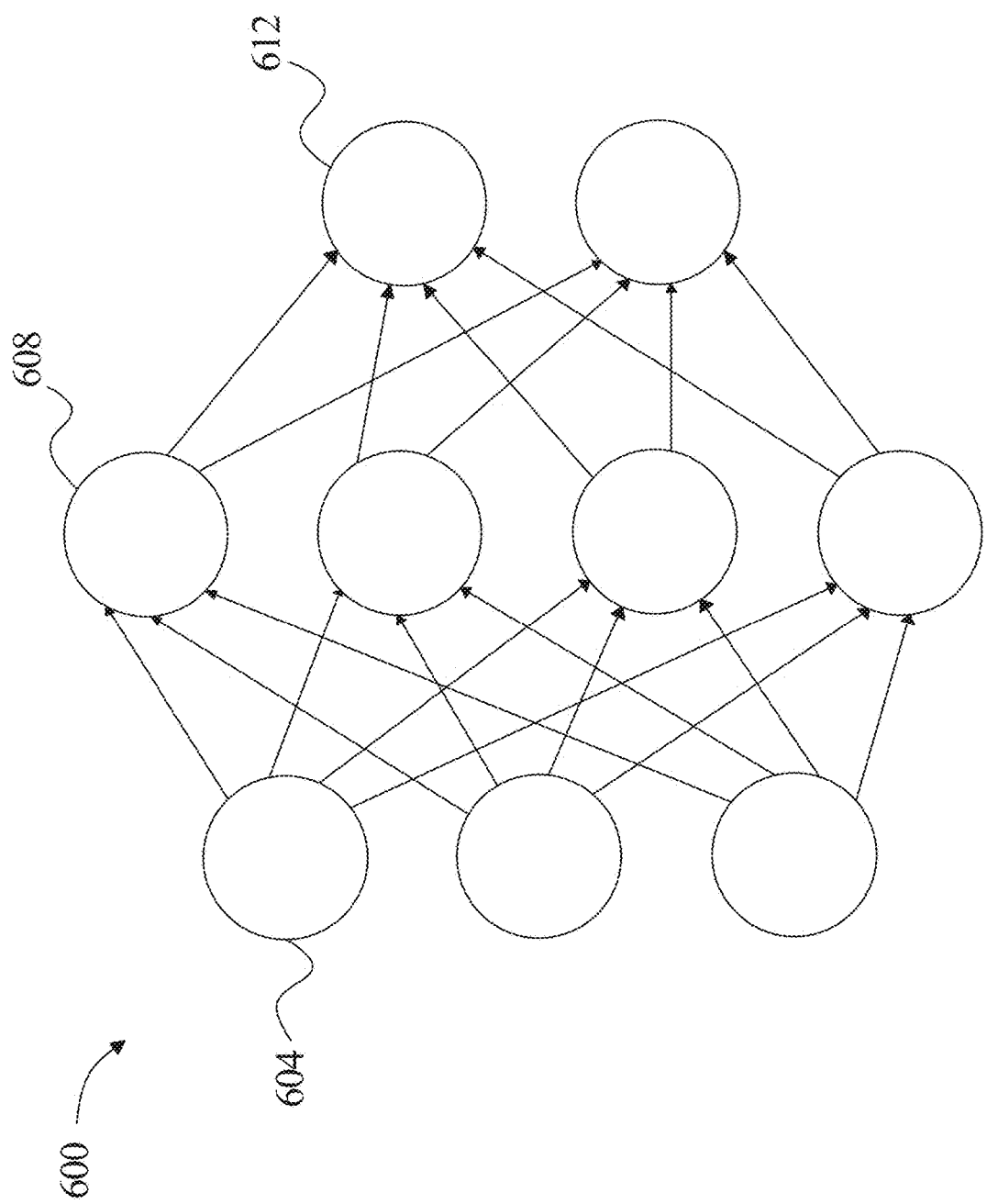
FIG. 6 illustrates a diagram of an exemplary neural network.

Referring now to FIG. 6, an exemplary embodiment of neural network 600 is illustrated. A neural network 600 also known as an artificial neural network, is a network of "nodes", or data structures having one or more inputs, one or more outputs, and a function determining outputs based on inputs. Such nodes may be organized in a network, such as without limitation a convolutional neural network, including an input layer of nodes 604, one or more intermediate layers 608, and an output layer of nodes 612. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network". As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel", along with one or more additional layers such as pooling layers, fully connected layers, and the like.

Figure 7:
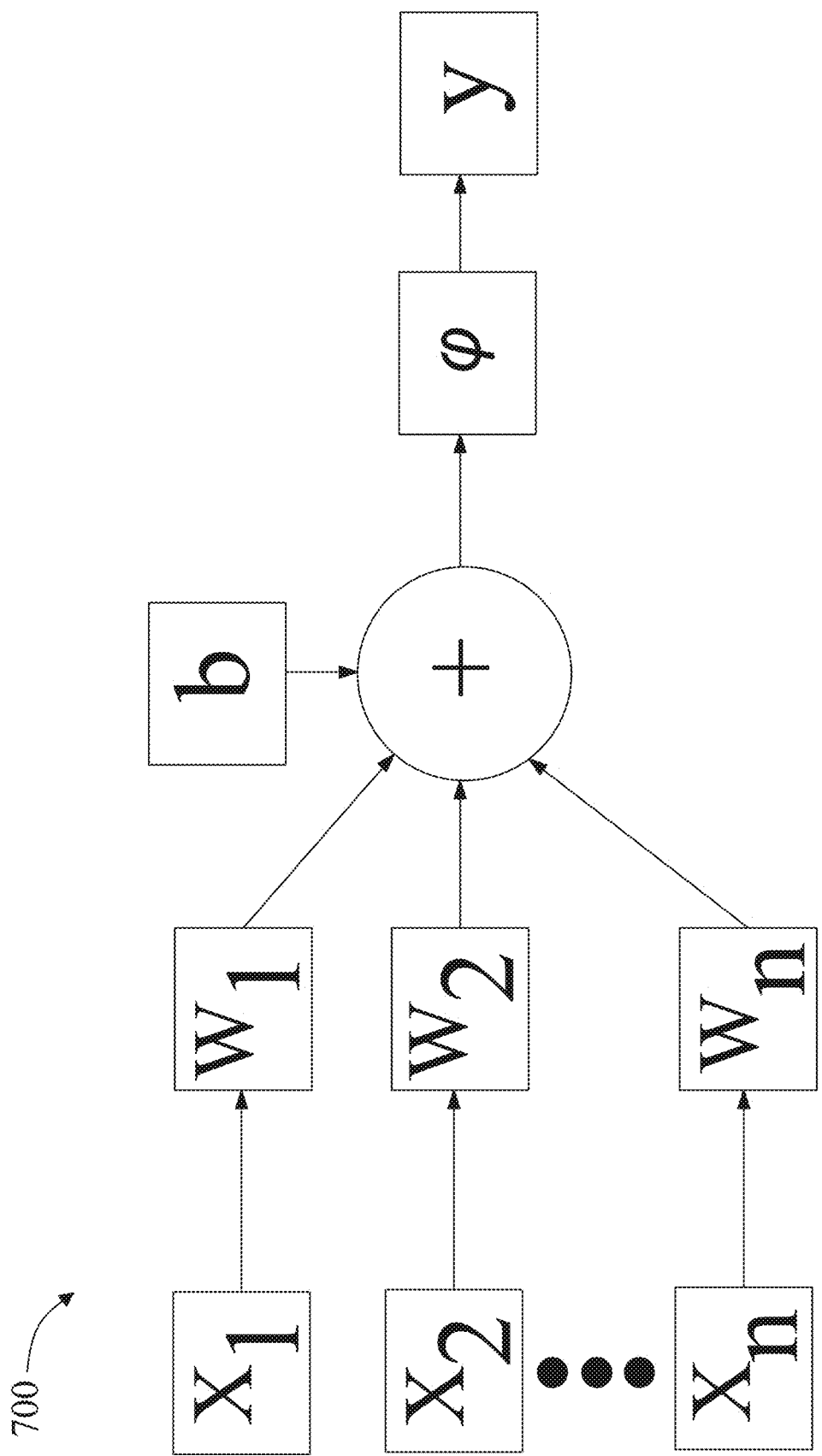
FIG. 7 illustrates a block diagram of an exemplary node in a neural network.

Referring now to FIG. 7, an exemplary embodiment of a node 700 of a neural network is illustrated. A node may include, without limitation a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x \text{ for } x \geq 0 \\ \alpha(e^x - 1) \text{ for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 8:
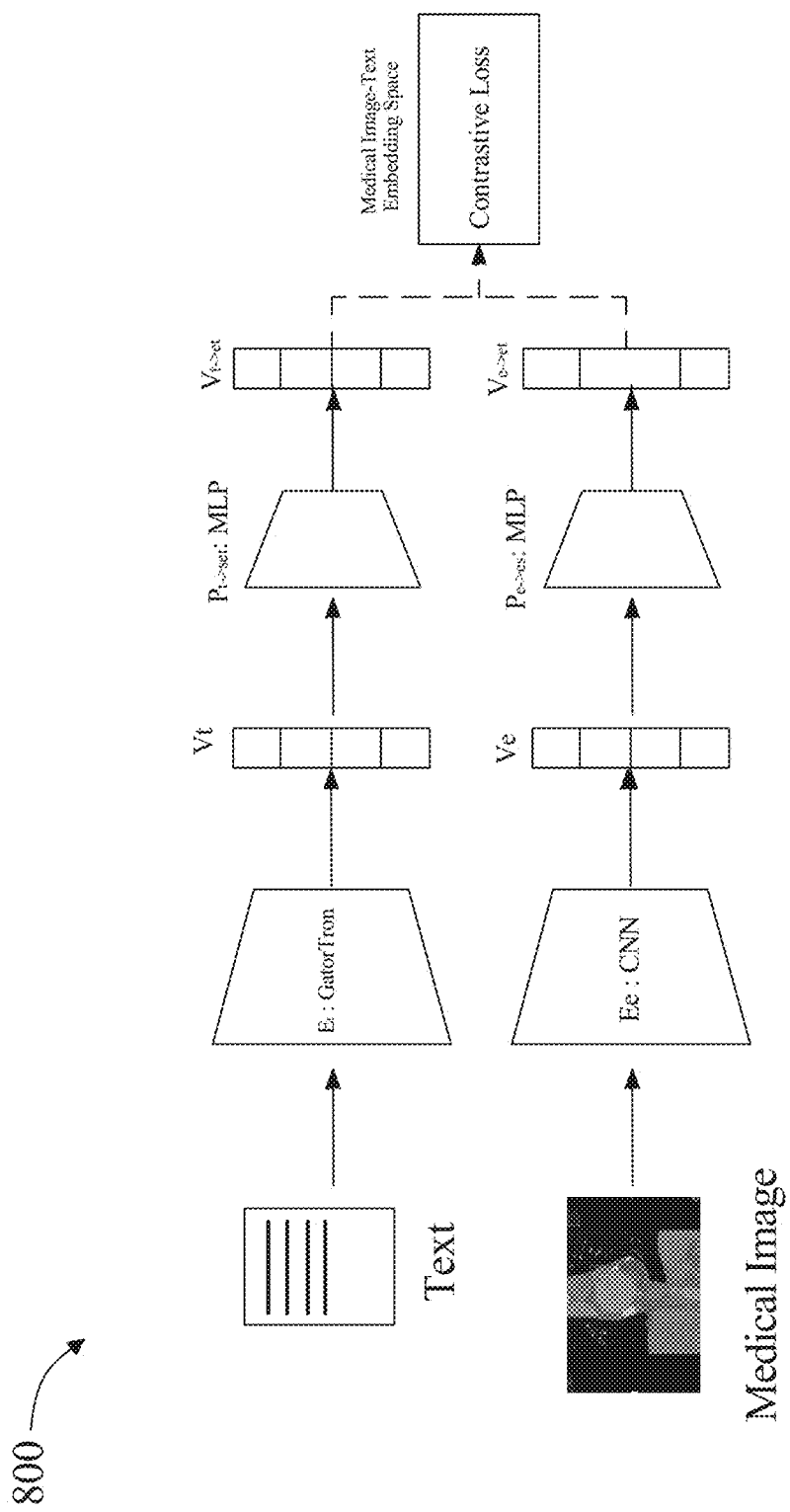
FIG. 8 illustrates a diagram of an exemplary Contrastive Visual Representation Learning from Text (ConVIRT) model of an implant machine-learning model.

Now referring to FIG. 8, an exemplary embodiment 800 of ConVIRT model that can be used to analyze subject data (e.g., current subject data 136 and historical subject data 112) and generate output datum 166 (e.g., is illustrated. Processor 104 may take a plurality of sets of subject data (e.g., current subject data 136 or historical subject data 112) that have an association with at least 50 patients and are considered in the vocabulary. In some cases, processor 104 may do a mapping of subject data (e.g., current subject data 136 and historical subject data 112) to maintain the same phenotypic information. To create output datum 166, processor 104 may randomly select one subject data (e.g., current subject data 136 and historical subject data 112) related to a given patient's timeline. In the Medical Image-Text model, processor 104 may pair electrocardiogram signals with unstructured text data obtained from a variety of medical sources, including medical image reports, ECHO reports, pathology reports, radiology reports, microbiology reports and clinical documents. These may be collectively referred to as subject data (e.g., current subject data 136 and historical subject data 112). Processor 104 may apply the contrastive learning between Medical Image and Text in joint Medical Image-Text Embedding space $\Omega_{et}$ $$v_e^i = E_e(x_e^i)$$

$$v_t^i = E_t(x_t^i)$$

$$v_{e\text{-}et}^i = P_{e \rightarrow et}(v_e^i)$$

$$v_{s\text{-}et}^i = P_{s \rightarrow et}(v_t^i)$$

In an embodiment, $L_{et}$ be the contrastive loss between Medical Image and Text, $L_i^{e \rightarrow t}$ be the contrastive loss directed from Medical Image to Text, and $L_i^{t \rightarrow e}$ be the contrastive loss directed from Text to Medical Image. Then, the loss for the Medical Image-Text model is given by:

$$L_{et} = \frac{1}{n} \sum_{i=1}^{N} (\lambda_{et} L_i^{e \rightarrow t} + (1 - \lambda_{et}) L_i^{t \rightarrow e})$$

$$L_i^{s \rightarrow t} = -\log \frac{\exp(s(v_{e\text{-}et}^i, v_{t\text{-}et}^i)/T)}{\sum_{i=1}^{N} \exp(s(v_{e\text{-}et}^i, v_{t\text{-}et}^k)/T)}$$

Counts for medical images and unique patients for each downstream task cohort.

$$L_i^{t \rightarrow e} = -\log \frac{\exp(s(v_{t\text{-}et}^i, v_{e\text{-}et}^i)/T)}{\sum_{K=1}^{N} \exp(s(v_{t\text{-}et}^i, v_{e\text{-}et}^k)/T)}$$

Figure 9:
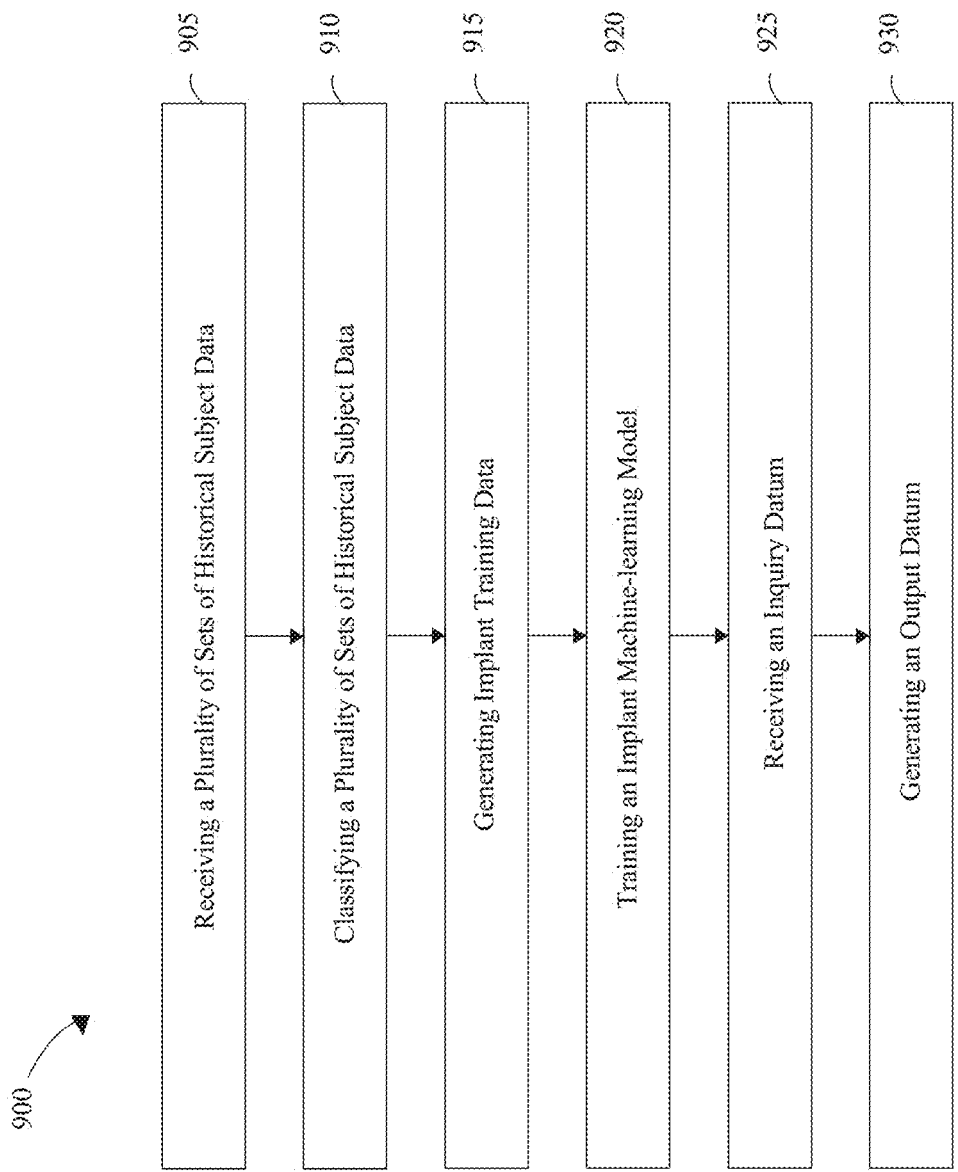
FIG. 9 illustrates a flow diagram of an exemplary method for leveraging a repository of images containing implant devices in a human body.

Referring now to FIG. 9, a flow diagram of an exemplary method 900 for leveraging a repository of images containing implant devices in a human body. Method 900 contains a step 905 of receiving, using at least a processor, a plurality of sets of historical subject data, wherein the plurality of sets of historical subject data includes historical image data and historical textual data related to an implant device implanted in a subject's body. This may be implemented as described with reference to FIGS. 1-8.

With continued reference to FIG. 9, method 900 contains a step 910 of classifying, using at least a processor, a plurality of sets of historical subject data into one or more implant cohorts. In some embodiments, classifying the plurality of sets of historical subject data into one or more implant cohorts may include generating implant cohort training data, wherein the implant cohort training data may include exemplary subject data correlated to exemplary implant cohorts, training an implant cohort classifier using the cohort training data and classifying the plurality of sets of historical subject data into one or more implant cohorts using the trained implant cohort classifier. This may be implemented as described with reference to FIGS. 1-8.

With continued reference to FIG. 9, method 900 contains a step 915 of generating, using at least a processor, implant training data using a plurality of sets of classified historical subject data in one or more implant cohorts, wherein the implant training data includes exemplary historical image data correlated to exemplary historical textual data. This may be implemented as described with reference to FIGS. 1-8.

With continued reference to FIG. 9, method 900 contains a step 920 of training, using at least a processor, an implant machine-learning model using implant training data. This may be implemented as described with reference to FIGS. 1-8.

With continued reference to FIG. 9, method 900 contains a step 925 of receiving, using at least a processor, an inquiry datum from a user, wherein the inquiry datum includes current subject data. This may be implemented as described with reference to FIGS. 1-8.

With continued reference to FIG. 9, method 900 contains a step 930 of generating, using at least a processor, an output datum as a function of an inquiry datum using a trained implant machine-learning model, wherein the output datum is related to a position of an implant device. In some embodiments, generating the output datum using the implant machine-learning model may include updating the implant training data as a function of an output of the implant cohort classifier and generating the output datum using the implant machine-learning model retrained with the updated implant training data. In some embodiments, generating the output datum may include generating an implant image as a function of the current subject data and the inquiry datum using an implant image generative model of the trained implant machine-learning model. In some embodiments, generating the output datum may include determining an implant position using a discriminative implant position model of the trained implant machine-learning model. In some embodiments, generating the output datum may include determining an organ position as a function of the implant position using a discriminative organ position model of the trained implant machine-learning model. In some embodiments, generating the output datum may include determining an anomaly datum as a function of the current subject data using an anomaly distribution model of the trained implant machine-learning model. In some embodiments, method 900 may further include generating, using the at least a processor, an alarm datum as a function of the anomaly datum and generating, using the at least a processor, a graphical user interface displaying the alarm datum. In some embodiments, method 900 may further include generating, using the at least a processor, subject cohort training data, wherein the subject cohort training data may include exemplary subject data correlated to exemplary subject cohorts, training, using the at least a processor, a subject cohort classifier using the subject cohort training data, classifying, using the at least a processor, the current subject data into one or more subject cohorts using the trained subject cohort classifier, updating, using the at least a processor, the implant training data to include the current subject data classified to the one or more subject cohorts using the trained subject cohort classifier and generating, using the at least a processor, the output datum using the implant machine-learning model retrained with the updated implant training data. These may be implemented as described with reference to FIGS. 1-8.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 10:
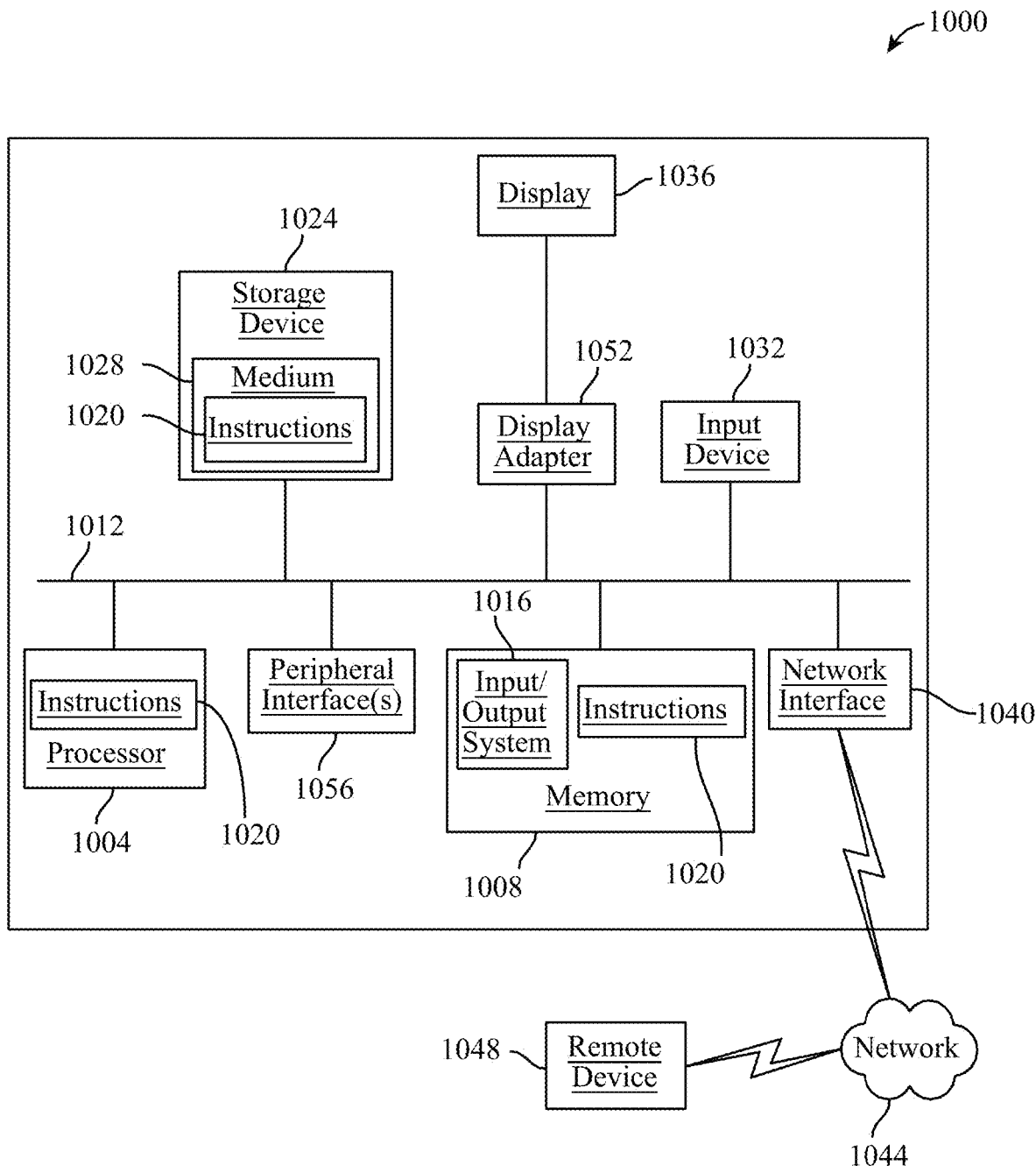
FIG. 10 is a block diagram of a computing system that can be used to implement any one or more of the methodologies disclosed herein and any one or more portions thereof.

FIG. 10 shows a diagrammatic representation of one embodiment of a computing device in the exemplary form of a computer system 1000 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1000 includes a processor 1004 and memory 1008 that communicate with each other, and with other components, via a bus 1012. Bus 1012 may include any of several types of bus structures including, but not limited to, memory bus, memory controller, a peripheral bus, a local bus, and any combinations thereof, using any of a variety of bus architectures.

Processor 1004 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1004 may be organized according to Von Neumann and/or Harvard architecture as a non-limiting example. Processor 1004 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 1008 may include various components (e.g., machine-readable media) including, but not limited to, a random-access memory component, a read only component, and any combinations thereof. In one example, a basic input/output system 1016 (BIOS), including basic routines that help to transfer information between elements within computer system 1000, such as during start-up, may be stored in memory 1008. Memory 1008 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Computer system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with computer system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for computer system 1000. In one example, software 1020 may reside, completely or partially, within machine-readable medium 1028. In another example, software 1020 may reside, completely or partially, within processor 1004.

Computer system 1000 may also include an input device 1032. In one example, a user of computer system 1000 may enter commands and/or other information into computer system 1000 via input device 1032. Examples of an input device 1032 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIREWIRE interface, a direct interface to bus 1012, and any combinations thereof. Input device 1032 may include a touch screen interface that may be a part of or separate from display device 1036, discussed further below. Input device 1032 may be utilized as a user selection device for selecting one or more graphical representations in a graphical interface as described above.

A user may also input commands and/or other information to computer system 1000 via storage device 1024 (e.g., a removable disk drive, a flash drive, etc.) and/or network interface device 1040. A network interface device, such as network interface device 1040, may be utilized for connecting computer system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or a wireless mode of communication. In general, any network topology may be used. Information (e.g., data, software 1020, etc.) may be communicated to and/or from computer system 1000 via network interface device 1040.

Computer system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, computer system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods and apparatuses according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for leveraging a repository of images containing implant devices in a human body, the apparatus comprising:
   at least a processor; and
   a memory communicatively connected to the at least a processor, wherein the memory contains instructions configuring the at least a processor to:
      receive a plurality of sets of historical subject data, wherein the plurality of sets of historical subject data comprises:
         historical image data and historical textual data related to an implant device implanted in a subject's body;
      classify the plurality of sets of historical subject data into one or more implant cohorts;
      generate implant training data using the plurality of sets of classified historical subject data in the one or more implant cohorts, wherein the implant training data comprises exemplary historical image data correlated to exemplary historical textual data;
      train an implant machine-learning model using the implant training data;
      receive an inquiry datum from a user, wherein the inquiry datum comprises current subject data; and
      generate an output datum as a function of the inquiry datum using the trained implant machine-learning model, wherein the output datum is related to a position of the implant device.

2. The apparatus of claim 1, wherein classifying the plurality of sets of historical subject data into one or more implant cohorts comprises:
   generating implant cohort training data, wherein the implant cohort training data comprises exemplary subject data correlated to exemplary implant cohorts;
   training an implant cohort classifier using the cohort training data;
   classifying the plurality of sets of historical subject data into one or more implant cohorts using the trained implant cohort classifier;
   updating the implant training data as a function of an output of the implant cohort classifier; and generating the output datum using the implant machine-learning model retrained with the updated implant training data.

3. The apparatus of claim 1, wherein generating the output datum comprises generating an implant image as a function of the current subject data and the inquiry datum using an implant image generative model of the trained implant machine-learning model.

4. The apparatus of claim 1, wherein generating the output datum comprises:
generating signature training data, wherein the signature training data comprises exemplary current subject data correlated to exemplary implant image signatures;
training a signature machine-learning model using the signature training data; and
determining an implant image signature of the current subject data using the signature machine-learning model.

5. The apparatus of claim 4, wherein generating the output datum comprises determining an implant position as a function of the implant image signature using a discriminative implant position model of the trained implant machine-learning model.

6. The apparatus of claim 5, wherein generating the output datum comprises determining an organ position as a function of the implant position using a discriminative organ position model of the trained implant machine-learning model.

7. The apparatus of claim 4, wherein generating the output datum comprises determining an anomaly datum as a function of the implant image signature using an anomaly distribution model of the trained implant machine-learning model.

8. The apparatus of claim 7, wherein the memory contains instructions configuring the at least a processor to:
generate an alarm datum as a function of the anomaly datum; and
generate a graphical user interface displaying the alarm datum.

9. The apparatus of claim 1, wherein the memory contains instructions configuring the at least a processor to:
generate subject cohort training data, wherein the subject cohort training data comprises exemplary subject data correlated to exemplary subject cohorts;
train a subject cohort classifier using the subject cohort training data;
classify the current subject data into one or more subject cohorts using the trained subject cohort classifier;
update the implant training data to comprise the current subject data classified to the one or more subject cohorts using the trained subject cohort classifier; and
generate the output datum using the implant machine-learning model retrained with the updated implant training data.

10. The apparatus of claim 1, wherein the memory contains instructions configuring the at least a processor to transmit the output datum to a remote device.

11. A method for leveraging a repository of images containing implant devices in a human body, the method comprising:
receiving, using at least a processor, a plurality of sets of historical subject data, wherein the plurality of sets of historical subject data comprises:
historical image data and historical textual data related to an implant device implanted in a subject's body;
classifying, using the at least a processor, the plurality of sets of historical subject data into one or more implant cohorts;
generating, using the at least a processor, implant training data using the plurality of sets of classified historical subject data in the one or more implant cohorts, wherein the implant training data comprises exemplary historical image data correlated to exemplary historical textual data;
training, using the at least a processor, an implant machine-learning model using the implant training data;
receiving, using the at least a processor, an inquiry datum from a user, wherein the inquiry datum comprises current subject data; and
generating, using the at least a processor, an output datum as a function of the inquiry datum using the trained implant machine-learning model, wherein the output datum is related to a position of the implant device.

12. The method of claim 11, wherein classifying the plurality of sets of historical subject data into one or more implant cohorts comprises:
generating implant cohort training data, wherein the implant cohort training data comprises exemplary subject data correlated to exemplary implant cohorts;
training an implant cohort classifier using the cohort training data;
classifying the plurality of sets of historical subject data into one or more implant cohorts using the trained implant cohort classifier;
updating the implant training data as a function of an output of the implant cohort classifier; and
generating the output datum using the implant machine-learning model retrained with the updated implant training data.

13. The method of claim 11, wherein generating the output datum comprises generating an implant image as a function of the current subject data and the inquiry datum using an implant image generative model of the trained implant machine-learning model.

14. The method of claim 11, wherein generating the output datum comprises:
generating signature training data, wherein the signature training data comprises exemplary current subject data correlated to exemplary implant image signatures;
training a signature machine-learning model using the signature training data; and
determining an implant image signature of the current subject data using the signature machine-learning model.

15. The method of claim 14, wherein generating the output datum comprises determining an implant position as a function of the implant image signature using a discriminative implant position model of the trained implant machine-learning model.

16. The method of claim 15, wherein generating the output datum comprises determining an organ position as a function of a discriminative organ position model of the implant position using the trained implant machine-learning model.

17. The method of claim 14, wherein generating the output datum comprises determining an anomaly datum as a function of the implant image signature using an anomaly distribution model of the trained implant machine-learning model.

18. The method of claim 17, further comprising:
generating, using the at least a processor, an alarm datum as a function of the anomaly datum; and
generating, using the at least a processor, a graphical user interface displaying the alarm datum.

19. The method of claim 11, further comprising:
generating, using the at least a processor, subject cohort training data, wherein the subject cohort training data comprises exemplary subject data correlated to exemplary subject cohorts;
training, using the at least a processor, a subject cohort classifier using the subject cohort training data;
classifying, using the at least a processor, the current subject data into one or more subject cohorts using the trained subject cohort classifier;
updating, using the at least a processor, the implant training data to comprise the current subject data classified to the one or more subject cohorts using the trained subject cohort classifier; and
generating, using the at least a processor, the output datum using the implant machine-learning model retrained with the updated implant training data.

20. The method of claim 11, further comprising:
transmitting, using the at least a processor, the output datum to a remote device.

* * * * *